United States Patent [19]
Duke et al.

[11] Patent Number: 5,830,463
[45] Date of Patent: Nov. 3, 1998

[54] YEAST-BASED DELIVERY VEHICLES

[75] Inventors: Richard C. Duke, Denver; Alex Franzusoff, Boulder; Donald Bellgrau, Denver, all of Colo.

[73] Assignee: University Technology Corporation, Boulder, Colo.

[21] Appl. No.: 340,185

[22] Filed: Nov. 15, 1994

Related U.S. Application Data

[63] Continuation-in-part of Ser. No. 88,322, Jul. 7, 1993, Pat. No. 5,413,914.
[51] Int. Cl.$^6$ .......................... C12N 15/00; C12N 15/09; A61K 48/00
[52] U.S. Cl. .................... 424/93.51; 424/93.5; 424/93.2; 435/320.1; 435/375; 435/172.3; 435/69.1
[58] Field of Search .............................. 435/320.1, 240.2, 435/6, 7.1, 172.3, 7.2, 7.31; 514/44; 935/62, 52, 55, 56, 57, 34, 32; 424/93.1, 93.2, 93.21, 93.51, 93.5; 536/23.74

[56] References Cited

U.S. PATENT DOCUMENTS

| | | | |
|---|---|---|---|
| 5,234,830 | 8/1993 | Oshima et al. | 435/252.3 |
| 5,399,346 | 3/1995 | Anderson et al. | 424/93.21 |
| 5,413,914 | 5/1995 | Franzusoff | 435/23 |

OTHER PUBLICATIONS

Baker et al., 1988, *Cell*, 54:335–344.
Bizzini et al., 1990, *FEMS Microbiol. Immunol.*, 64:155–168.
Bourdette et al., 1994, *J. Immunol.*, 152:2510–2519.
Brake et al., 1984, *Proc. Natl. Acad. Sci. USA*, 81:4642–4646.
Chou et al., 1994, *J. Immunol.*, 152:2520–2529.
Cohen, 1994, *Science*, 264:1660.
Engelhardt et al., 1994, *Hum. Gene Ther*, 5:1217–1229.
Fattal–German et al., 1992, *Develop. Biol. Standard.*, 77:115–120.
Rabinovich et al., 1994, *Science*, 265:1401–1404.
Sanchez–Pescador et al., 1985, *Science*, 227:484–492.
Stern et al., 1992, *Cell*, 68:465–477.
Suda et al., 1993, *Cell*, 75:1169–1178.
Marshall, E. "Gene Therapy's Growing Pains," *Science*, vol. 269: 1050–1055, Aug. 25, 1995.
Davies et al., 1992, *Nucleic Acids Res.*, 20(11):2693–2698.
Demmer et al., 1993, *J. Immunol.*, 150(12):5371–5378.
Franzusoff et al., 1995, *J. Biol. Chem.*, 270(7):3154–3159.
Gnirke et al., 1991, *EMBO J.*, 10(7):1629–1634.
Gobin et al., 1995, *Gene*, 163:27–33.
Hatsuyama et al., 1994, *Plant Cell Physiol.*, 35(1):93–98.
Ketner et al., 1994, *Proc. Natl. Acad. Sci. USA*, 91:6186–6190.
Markie et al., 1993, *Somat. Cell Mol. Genet.*, 19(2):161–169.
Mullen et al., 1994, *Plant Physiol.*, 105:113 (Abstr. 606).
Pachnis et al., 1990, *Proc. Natl. Acad. Sci. USA*, 87:5109–5113.
Peterson et al., 1993, *Proc. Natl. Acad. Sci. USA*, 90:11207–11211.
Fujita, et al. "Studies in the development of Japanese encephalitis vaccine: Expression of virus envelope glycoprotein V3 gene in yeast". *Bull. WHO.*, vol. 65, No. 3, 265–424, Sep. 8, 1997.
Valenzuela, et al. "Antigen engineering in yeast: Synthesis and assembly of hybrid hepatitis B surface antigen–Herpes simplex 1 gD particles", *Bio/Technology*, vol. 3, 323–326, Apr. 1985.
Fearon, et al. "Interleukin–2 production by tumor cells bypasses T Helper Function in the Generation of an Antitumor Response", *Cell*, vol. 60, 397–403, Feb. 9, 1990.
Mulligan, et al. "The Basic Science of Gene Therapy". *Science*, vol. 260, 926–930, May 14, 1993.
Brown, D. "Gene Therapy 'Oversold' By Researchers, Journalists". *The Washington Post*, A22, Dec. 8, 1995.
Coghlan, A. "Gene dream fades away". *New Scientist*, pp. 14–15, Nov. 25, 1995.
Bachmann, et al. "In vivo versus in vitro assays for assessment of T– and B– cell function". *Current Opinion in Immunology*, vol. 6, 320–326, Jun. 1994.

*Primary Examiner*—Jasemine C. Chambers
*Assistant Examiner*—Karen M. Hauda
*Attorney, Agent, or Firm*—Sheridan Ross P.C.

[57] ABSTRACT

The present invention includes yeast vehicles and their use as delivery vehicles. Yeast vehicles include a yeast portion and a heterologous compound. Such yeast vehicles can be used to protect animals from disease and to otherwise carry compounds to given cell types. Examples of yeast vehicles include gene delivery vehicles, drug delivery vehicles, and immunomodulatory vehicles. Immunomodulatory vehicles are capable of modulating an immune response. When stimulating an immune response, such yeast vehicles effect cell-mediated as well as humoral immunity.

12 Claims, 3 Drawing Sheets

YEAST-BASED DELIVERY VEHICLES

CROSS-REFERENCE TO RELATED APPLICATIONS

The present application is a continuation-in-part of U.S. patent application Ser. No. 08/088,322, entitled "Yeast Assay to Identify Inhibitors of Dibasic Amino Acid Processing Endoproteases", filed Jul. 7, 1993, patented as U.S. Pat. No. 5,413,914 which is incorporated by reference herein in its entirety.

This invention was made at least in part with government support under Grant No. AI 74747 awarded by the National Institutes of Health. The government has certain rights to this invention.

FIELD OF THE INVENTION

The present invention is directed to yeast-based delivery vehicles and their use to deliver a variety of compounds to a variety of cell types. Yeast vehicles of the present invention can be used, for example, as drug delivery vehicles, gene delivery vehicles or immunomodulatory vehicles.

BACKGROUND OF THE INVENTION

Vaccines are one of the most cost-effective measures available to the health care industry. There remains, however, an urgent need to develop safe and effective vaccines and adjuvants for a variety of diseases, including those due to infection by pathogenic agents, cancers, genetic defects and other disorders of the immune system. Rabinovich et al., 1994, Science 265, 1401–1404, for example, state that there is still a need for safe and heat-stable vaccines that can be administered orally and that need only be administered a few times, preferably early in life. Also preferred are combination vaccines that can protect individuals from more than one disease, as well as vaccines that do not require an adjuvant and that can elicit mucosal immunity. To date very few, if any, vaccines meet all of these criteria.

Subunit vaccines, the development of which was made possible by recombinant DNA technology, have been disappointing to date as they exhibit only limited immunogenicity. One example is the recent clinical testing of several HIV (human immunodeficiency virus) subunit vaccines which has been stopped due not only to limited efficacy of the vaccines but also because in some cases immunized individuals showed accelerated disease progression when they were subsequently exposed to HIV; see, for example, Cohen, 1994, Science 264, 1839; and Cohen, 1994, Science 264, 1660. One disadvantage of subunit vaccines, as well as of killed virus and recombinant live virus vaccines, is that while they appear to stimulate a strong humoral immune response, they fail to elicit protective cellular immunity. A major conclusion at the 1994 International AIDS Conference was that there remains a need for a cytotoxic T cell-mediated response to prevent, or reduce, HIV infectivity, which to date is lacking in vaccines in the clinic. In addition, HIV vaccines tested to date have failed to elicit immunity at the mucosal surfaces where primary HIV infection occurs.

Furthermore, the only adjuvants approved for use in the United States are the aluminum salts aluminum hydroxide and aluminum phosphate, neither of which stimulates cell-mediated immunity. In addition, aluminum salt formulations cannot be frozen or lyophilized, and such adjuvants are not effective with all antigens.

Yeast have been used in the production of subunit protein vaccines, including some of those tested in the aforementioned HIV vaccine trials. Yeast have also been fed to animals prior to immunization to try to prime the immune response in a non-specific manner (i.e., to stimulate phagocytosis as well as the production of complement and interferon). The results have been ambiguous, and such protocols have not generated protective cellular immunity; see, for example, Fattal-German et al., 1992, Dev. Biol. Stand. 77, 115–120; Bizzini et al., 1990, FEMS Microbiol. Immunol. 2, 155–167.

In addition to vaccines, many gene and drug therapies require efficient and specific delivery vehicles to ensure the greatest possible benefit. Lack of an adequate delivery vehicle is a major roadblock to the application of gene therapy and significantly limits the therapeutic potential of many drugs. For example, recent reports have indicated that adenovirus vectors, which are currently being tested in the clinic for gene therapy applications, are stimulating undesirable immune and inflammatory responses and do not appear to be integrating in a desired manner; see, for example, Engelhardt et al., 1994, Human Gene Therapy 5, 1217–1229 and references cited therein.

As such, there remains a need for compositions that effectively modulate immunity, either to stimulate an immune response, such as in the case of a vaccine, or to suppress an undesirable immune response, such as an autoimmune response or an excessive inflammatory response. There also remains a need for improved gene and drug delivery vehicles.

SUMMARY OF THE INVENTION

The present invention includes the surprising discovery that compounds carried by yeast trigger cell-mediated immunity, without the need for an adjuvant. As such, the present invention includes yeast-based vaccines that meet the criteria cited in the background section. That is, yeast vehicles of the present invention comprising nonpathogenic yeast carrying at least one compound capable of modulating an immune response (a) are efficacious at stimulating cell-mediated, as well as humoral, immunity, (b) are safe, (c) have long shelf-lives (i.e., are stable to storage for long periods of time), (d) can be administered orally, (e) require very few, if any, booster immunizations, (f) can be combination vaccines in that they can be engineered to carry multiple compounds, (g) do not require an adjuvant, and (h) can elicit immunity at mucosal surfaces.

The present invention includes a method to protect an organism from a disease, which includes the step of administering to the organism a composition comprising a yeast vehicle which includes a yeast portion and a compound capable of protecting the organism from that disease. Such a compound is carried by and is heterologous to the yeast portion. Preferred organisms to protect include animals and plants. Yeast vehicles can either deliver compounds to a cell type that is capable of adsorbing yeast or can be engineered to selectively deliver compounds to desired cell types. Compositions can be administered in vivo or ex vivo.

Preferred compounds to include in yeast vehicles of the present invention include nucleic acid molecules, peptides, proteins, carbohydrates, lipids, inorganic protective compounds, other organic protective compounds and mixtures of such compounds. Yeast vehicles of the present invention can include compounds that protect organisms from a variety of diseases, depending on the nature of the compound, including genetic defects, diseases caused by infectious agents and other metabolic disorders.

Preferred yeast vehicles of the present invention are able to modulate the immune response of an organism. Such yeast vehicles can be designed either to stimulate a protective immune response or to suppress a harmful immune response. Such yeast vehicles are particularly useful because they stimulate cell-mediated immune responses as well as humoral immune responses. As such, a preferred method of the present invention is a method to modulate a cell-mediated immune response in an animal which includes the step of administering to the animal a composition comprising a yeast vehicle of the present invention capable of modulating an immune response in the animal.

The present invention also includes a method to deliver a compound to a given (i.e., desired) cell type which includes the step of administering to a population of cells including that cell type a composition comprising a yeast vehicle including a yeast portion and the compound. The compound is carried by and is heterologous to the yeast portion, and the yeast vehicle is capable of targeting the compound to that cell type. The population of cells can comprise an organism, such as a plant or an animal. The composition can be administered in vivo, ex vivo or in vitro.

One embodiment of the present invention is a method to deliver a compound to a given cell type which includes the step of administering to a population of cells including that cell type a composition comprising a yeast vehicle transformed with a heterologous nucleic acid molecule capable of expressing that compound. In this embodiment, the yeast vehicle is able to fuse with the given cell type, thereby delivering the compound to that cell type.

Also included in the present invention is a method to transfer a nucleic acid molecule into a given cell type that includes the step of administering to a population of cells including that cell type a composition comprising a yeast vehicle transformed with that nucleic acid molecule, wherein the vehicle is capable of fusing with that cell type and of transferring the nucleic acid molecule into that cell type. The method can be accomplished in vivo, ex vivo or in vitro and can, in one embodiment, effect gene therapy.

The present invention also includes a composition comprising a yeast vehicle having a heterologous component positioned on the yeast vehicle's outer membrane in such a manner that the component is capable of targeting the yeast vehicle to a given cell type, the yeast vehicle also carrying a heterologous compound. In preferred embodiments, the yeast vehicle is transformed with one or more nucleic acid molecules encoding a heterologous component and/or a heterologous compound in such a manner that the component and/or compound is/are expressed by the yeast vehicle.

Also included in the present invention is a composition comprising a yeast vehicle carrying at least two heterologous compounds, wherein the yeast vehicle is capable of protecting an organism from a disease. The compounds preferably are expressed by the yeast vehicle which is transformed with one or more nucleic acid molecules encoding the compounds. In one embodiment, the compounds are capable of modulating an immune response, one of the compounds preferably being a biological response modifier. In a preferred embodiment, the yeast vehicle also includes a heterologous component positioned on the yeast vehicle's outer membrane in such a manner that the component is capable of targeting the yeast vehicle to a given cell type.

The present invention also includes a composition comprising (a) a yeast vehicle having at least one compound heterologous to the yeast vehicle and (b) a pharmaceutically acceptable excipient. Such a yeast vehicle preferably is a gene delivery vehicle, a drug delivery vehicle, and/or a immunomodulatory yeast vehicle.

Also included in the present invention is a yeast vehicle comprising a yeast strain capable of producing a heterologous precursor protein having a dibasic amino acid processing site. Such a yeast strain is capable of correctly processing the precursor protein into at least one cleavage protein.

Another embodiment of the present invention is a method to test the ability of a yeast vehicle of the present invention to elicit a protective immune response against a disease, wherein the test is conducted in a surrogate animal model (i.e., a model comprising a surrogate animal). Such a method includes the steps of (a) treating the animal with a composition comprising a yeast vehicle transformed with a heterologous nucleic acid molecule that expresses a compound being tested for the ability to elicit a protective immune response to produce a treated animal; (b) administering to the treated animal a tumor cell that expresses the same compound (preferably because the tumor cell is transformed with a nucleic acid molecule encoding the compound), such a tumor cell being lethal to an untreated animal; and (c) determining if the treated animal survives the step of administering the tumor cell. Survival of the treated animal indicates that the yeast vehicle is capable of eliciting a protective immune response against the disease.

DETAILED DESCRIPTION OF THE INVENTION

Figure 1:
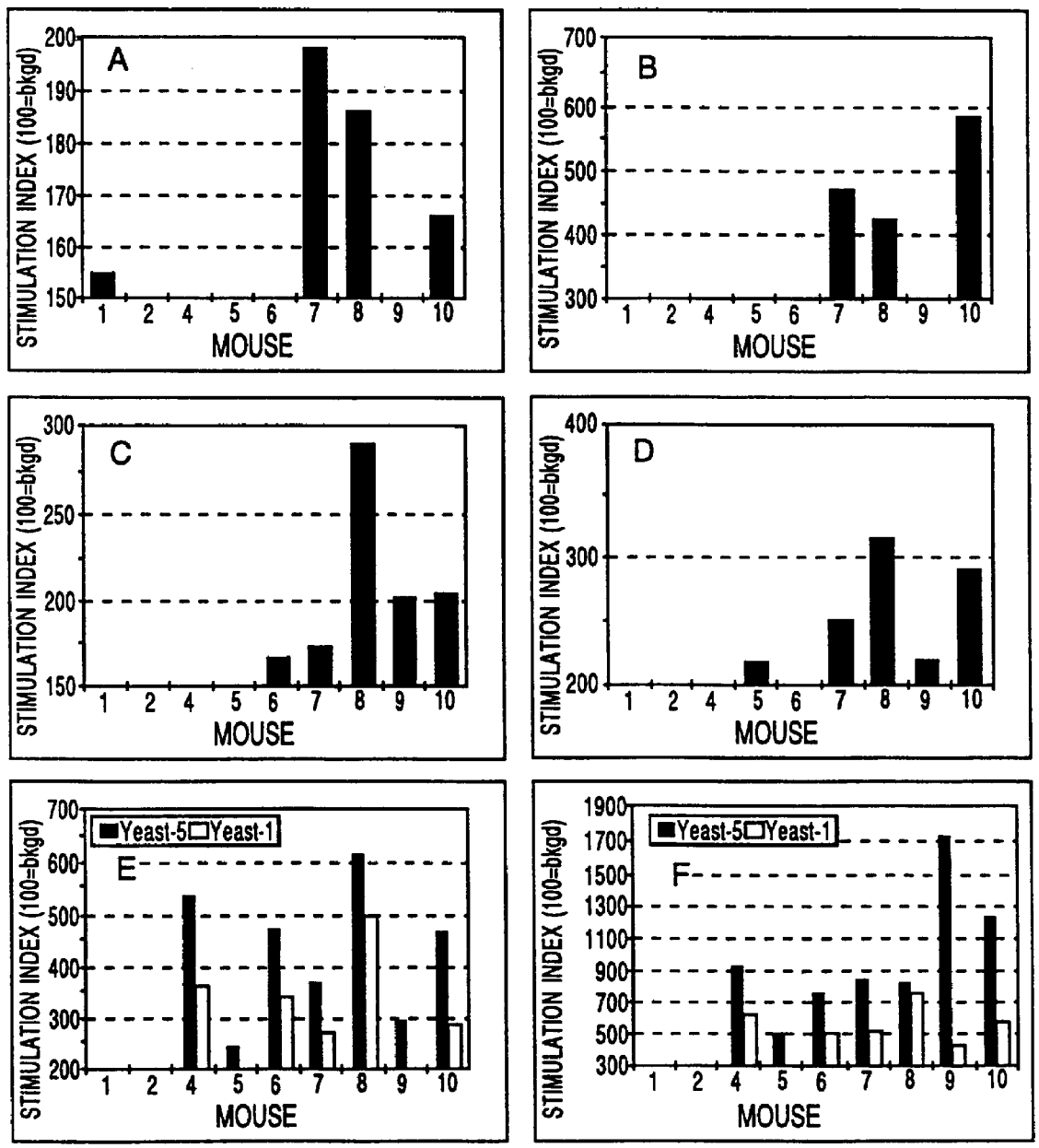
FIGS. 1A–F includes graphs depicting in vitro proliferation of T cells isolated from mice administered yeast vehicles of the present invention.

The present invention includes yeast-based delivery vehicles (also referred to herein as yeast vehicles) and their use for the in vivo, ex vivo and/or in vitro delivery of compounds to cells. That yeast vehicles are particularly useful delivery vehicles with certain advantages not shared by other delivery vehicles is a surprising aspect of the present invention, and the inventors are not aware of any use of yeast as delivery vehicles prior to the present invention.

Yeast-based delivery vehicles of the present invention have a number of advantages including, but not limited to, ease of manipulation using recombinant and/or classical genetic techniques, ability to target compounds to cells that naturally adsorb yeast cells and ability to genetically engineer yeast to target compounds to other desired cell types. In a preferred embodiment, such yeast vehicles are able to bind and fuse with the desired cell type to form syncytia, thereby delivering the compound in an effective manner to a high percentage of targeted cells. Nonpathogenic yeast strains also represent safe delivery vehicles, and a number of yeast strains, including *Saccharomyces cerevisiae*, have been designated by the U.S. Food and Drug Administration as being GRAS (i.e., Generally Recognized as Safe) for use in food products. Yeast vehicles of the present invention can be administered by a variety of routes, as discussed in detail below, including orally.

Yeast vehicles are also advantageous because they can carry one or more compounds and can be genetically engineered to carry one or more nucleic acid molecules capable of effecting gene therapy and/or of encoding one or more proteins and/or RNA molecules. A yeast vehicle can carry a compound within the yeast vehicle, on the yeast membrane surface, spanning the yeast membrane, within the yeast periplasm, and combinations thereof. As such, at least some of the compound stays associated with the yeast vehicle at least until the vehicle reaches its target, or site of action (e.g., the bloodstream, interstitial tissue, or a cell), at which point it is also possible that a compound carried by the yeast vehicle may, at least in part, be released (e.g., leak out) from the vehicle.

One particularly surprising, as well as very significant, advantage of a yeast vehicle of the present invention is that, when used in an embodiment to modulate (i.e., regulate) the immune response, administration to an animal of an antigen-carrying yeast vehicle induces the animal to produce a cell-mediated as well as a humoral immune response against that antigen, apparently without also causing harmful side effects. Such a property has been much sought after without a great deal of success using killed microorganisms (e.g., bacteria or viruses), subunit vaccines, vaccines carried in viral or bacterial vehicles, and vaccines that include an adjuvant. While not being bound by theory, it is believed that the yeast portion of the yeast vehicle is acting as an adjuvant to stimulate immunity in response to the antigen and that because the yeast is actually carrying the antigen, the yeast is able to effect class I MHC (as shown, for example, by the production of cytotoxic T cells that can target the antigen) as well as class II MHC-mediated immunity (as shown, for example, by antibody production) against the antigen. It is to be noted that, as used herein, an antigen refers to any compound that is capable of producing an immune response when administered to an organism, preferably leading to a protective response. Antigens can include immunogens and toleragens.

Furthermore, yeast vehicles of the present invention apparently do not cause significant side effects such as accompany other adjuvants. Even immunodeficient (e.g., SCID) mice that are administered a yeast vehicle of the present invention comprising an HIV gp160 gene inserted into a *S. cerevisiae* yeast strain are not adversely affected by the yeast vehicle. This finding is particularly relevant to use of yeast vehicles of the present invention to protect immunodeficient, as well as immunocompetent, individuals from disease.

Moreover, as will be discussed in detail below, yeast vehicles of the present invention can modulate an immune response not only to stimulate (i.e., elicit, produce, and/or enhance) a protective immune response but also to suppress (i.e., reduce, inhibit, block) an overactive, or harmful, immune response. Depending on how they are engineered, yeast vehicles of the present invention can also preferentially enhance, or amplify, cell-mediated immunity compared to humoral immunity or vice versa.

One embodiment of the present invention is a method to protect an organism from a disease by administering to that organism a composition that includes a yeast vehicle that includes a yeast portion and a compound capable of protecting the organism from that disease. It is to be noted that the term "a" or "an" entity refers to one or more of that entity. As such, the terms "a" (or "an"), "one or more" and "at least one" can be used interchangeably herein. In accordance with the present invention, a compound is carried by the yeast portion of the vehicle, a characteristic which is also referred to herein as the yeast vehicle carries the compound. The compound carried by the yeast vehicle (more specifically by the yeast portion) is heterologous to the yeast portion of the vehicle, meaning that the compound is derived from a species or subspecies of yeast or other organism that is different from the strain (i.e., species, subspecies) of yeast used in the production of the yeast portion of the vehicle. Such a compound may be an organic or inorganic compound not found naturally in the yeast strain used in the production of the vehicle and, in a preferred embodiment, can be a nucleic acid molecule that is heterologous to the yeast strain used in the production of the vehicle, and/or a compound encoded by such a nucleic acid molecule (e.g., an RNA molecule or a protein). As discussed in more detail below, organisms that can be protected from a disease are organisms that are susceptible to such a disease and preferably include animals and plants.

As used herein, a yeast vehicle of the present invention includes both a yeast portion and a compound that is carried by the yeast portion. A yeast portion of a yeast vehicle of the present invention refers to any yeast strain or derivative thereof that can be used to carry a desired compound to an animal or a plant. As such, the yeast portion of a yeast vehicle can include, but is not limited to, an intact yeast microorganism (i.e., a yeast cell having all its components including a cell wall), a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), or a yeast membrane particle. Yeast ghosts are typically produced by resealing a permeabilized or lysed cell and can, but need not, contain at least some of the organelles of that cell. A yeast membrane particle refers to a yeast membrane that carries a desired compound, but that lacks a natural nucleus or cytoplasm. The membrane can be of any size, including sizes ranging from the size of a natural yeast membrane to microparticles produced by sonication or other membrane disruption methods known to those skilled in the art, followed by resealing. Compounds can be carried inside the membrane, on the surface of the membrane, or combinations thereof (i.e., the compound can be both inside and outside the membrane and/or spanning the membrane of the yeast membrane particle). A preferred yeast membrane particle is a recombinant yeast membrane particle which can be an intact, disrupted, or disrupted and resealed yeast membrane that includes at least one desired compound on the surface of the membrane or at least partially embedded within the membrane. An example of a yeast membrane particle is a yeast membrane carrying an antigen of an infectious agent on its surface or at least partially embedded within the membrane such that the yeast membrane particle, when administered to an animal, stimulates a desired (i.e., protective) immune response against the infectious agent.

Any yeast strain can be used to produce a yeast vehicle of the present invention. Yeast are unicellular microorganisms that belong to one of three classes: Ascomycetes, Basidiomycetes and Fungi Imperfecti. While pathogenic yeast strains, or nonpathogenic mutants thereof, have been used in the past as adjuvants or as biological response modifiers and can be used in accordance with the present invention, nonpathogenic yeast strains are preferred. Preferred genera of yeast strains include Saccharomyces, Candida, Cryptococcus, Hansenula, Kluyveromyces, Pichia, Rhodotorula, Schizosaccharomyces and Yarrowia, with Saccharomyces, Candida, Hansenula, Pichia and Schizosaccharomyces being more preferred, and with Saccharomyces being particularly preferred. Preferred species of yeast strains include *Saccharomyces cerevisiae, saccharomyces carlsbergensis, Candida albicans, Candida kefyr, Candida tropicalis, Cryptococcus laurentii, Cryptococcus neoformans, Hansenula anomala, Hansenula polymorpha,*

*Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are meant to be included within the aforementioned species. More preferred yeast species include *S. cerevisiae, C. albicans, H. polymorpha, P. pastoris* and *S. pombe. S. cerevisiae* is particularly preferred due to it being relatively easy to manipulate and being GRAS. One embodiment of the present invention is a yeast strain that is capable of replicating plasmids to a particularly high copy number, such as a *S. cerevisiae* cir° strain.

Yeast vehicles of the present invention can carry a wide variety of compounds capable of protecting an animal or a plant from disease. As used herein, and as discussed in more detail below, a compound capable of protecting an animal or plant from disease is a compound that when administered to an animal or plant can prevent a disease from occurring and/or cure or alleviate disease symptoms or cause. A disease can refer to any deviation from normal health of any part of an organism and as such can include conditions in which disease symptoms are manifest as well as conditions in which a deviation (e.g., infection, gene mutation, etc.) has occurred but symptoms are not yet manifest. Yeast vehicles of the present invention are particularly useful as vehicles to deliver compounds to combat one or more diseases afflicting an animal or plant. Examples of diseases from which to protect an animal or plant include, but are not limited to, infections, genetic defects and other metabolic disorders. Such classes of diseases can lead to abnormal cell growth (e.g., benign or malignant neoplasia, hyperplastic syndromes), degenerative processes, and/or immunological defects as well as to a number of other disorders.

One embodiment of the present invention is the use of yeast vehicles to protect an organism from a disease caused by an infectious agent. An infectious agent can be any agent that can infect an organism (preferably an animal or a plant) and cause disease. Such disease may develop rapidly or after a long period of time. Suitable infectious agents against which to protect organisms using yeast vehicles of the present invention include, but are not limited to, viroids, prions, viruses, bacteria, fungi (including yeast), protozoa (e.g., amebas, flagellates and sporozoa), helminths and ectoparasites. It is within the scope of the present invention to protect an animal against more than one infectious agent. It should also be noted that although some infectious agents have not been definitively classified into one of these groups, such infectious agents are also included in the present invention.

Preferred yeast vehicles are capable of protecting an animal from infection by infectious agents that damage, for example, the aural, dermal, enteric, immune, neural, oral/dental, reproductive, respiratory and/or urinary systems of animals. Such infectious agents include, but are not limited to, adenoviruses, arena viruses, bunyaviruses, coronaviruses, hepadnaviruses, herpes viruses, myxoviruses, oncogenic viruses, orthomyxoviruses, papovaviruses, paramyxoviruses, parvoviruses, picornaviruses, pox viruses, rabies viruses, reoviruses, rhabdoviruses, rubella viruses, togaviruses, plant viruses, Aspergillus, Brugia, Candida, Chlamydia, Coccidia, Cryptococcus, Dirofilaria, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma and Vibriocholerae as well as other infectious agents that cause opportunistic infections in animals that are immunodeficient or otherwise immunosuppressed. Additional preferred infectious agents include other harmful microorganisms found in brackish water, food contaminants and wounds.

Preferred viruses from which to protect organisms using yeast vehicles of the present invention include Coxsackie viruses, cytomegaloviruses, Epstein-Barr viruses, flaviviruses, hepatitis viruses, herpes viruses, influenza viruses, measles viruses, mumps viruses, papilloma viruses, parainfluenza viruses, parvoviruses, rabies viruses, respiratory syncytial viruses, retroviruses and varicella viruses.

Retroviruses, herpes viruses, and hepatitis viruses are more preferred, with leukemia, lymphotrophic, sarcoma and lentiviruses being even more preferred, as are other immunodeficiency or tumor viruses. Particularly preferred lymphotrophic viruses from which to protect organisms include T-lymphotrophic viruses, such as human T-cell lymphotrophic viruses (HTLVs, such as HTLV-I and HTLV-II), bovine leukemia viruses (BLVS) and feline leukemia viruses (FLVs). Particularly preferred lentiviruses include human (HIV), simian (SIV), feline (FIV) and canine (CIV) immunodeficiency viruses, with HIV-1 and HIV-2 being even more preferred.

Another embodiment is the use of yeast vehicles of the present invention to protect an animal from other diseases, such as those caused by genetic and/or metabolic defects. Yeast vehicles of the present invention are capable of transferring a nucleic acid molecule that comprises a gene, or a portion thereof, to an appropriate cell type in order to correct a genetic defect. As used herein, genetic defects include mutations affecting the germ line as well as somatic mutations, such as those that cause many forms of cancer as well as autoimmune diseases and other immuno-defective disorders. Yeast vehicles of the present invention can be used to correct any genetic defect by using the yeast's natural propensity for certain cell types and/or, as appropriate, by targeting the yeast vehicles to additional cell types. Genetic defects from which to protect organisms include, but are not limited to, blood factor disorders, cancers linked to a genetic defect (including oncogene activation, loss of tumor suppressor gene function), cystic fibrosis, Gaucher's disease, hemoglobinopathies (such as thalassemias and sickle cell anemia), hypercholesterolemia, Lesch Nyhan syndrome, muscular dystrophy, signalling protein disorders, Tay Sachs disease, and combinations of such defects (i.e., mixtures or combinations thereof). As used herein, gene therapy includes methods to "turn on" the expression of desired genes as well as methods to "turn off" harmful gene expression. As such, gene therapy includes the introduction of regulatory regions and/or coding regions to desired cell types in order to correct genetic defects resulting from deregulation of gene expression as well as from loss of functional coding regions.

Additional diseases from which to protect an animal using a yeast vehicle of the present invention include, but are not limited to, allergies, anemias, autoimmune diseases (e.g., diabetes, multiple sclerosis, rheumatoid arthritis), cancers, cardiovascular diseases, graft versus host disease (GVHD), hematopoietic disorders, immunodeficiency diseases, immunoproliferative diseases, immunosuppressive disorders, inflammatory diseases, jaundice, myelosuppressive disorders, rejection of allografts or xenografts, septic shock, other immunological defects and combinations thereof. Many of these diseases can be acute or chronic. Examples of particular diseases from which organisms can be protected using yeast vehicles of the present invention are disclosed herein. It is to be noted that such examples are intended only as such and do not limit the wide variety of diseases against which appropriately designed yeast vehicles of the present invention can protect animals or plants.

There is a wide variety of compounds that can be included in yeast vehicles of the present invention in order to protect an animal from a disease, and it is within the scope of the present invention that a yeast vehicle can include one or more of such compounds. Such compounds can be of a variety of chemical structures and can have a variety of functions. It is to be noted that when using live yeast vehicles, it is important to select compounds that do not substantially harm the yeast.

In one embodiment, suitable compounds to be carried in yeast vehicles of the present invention include compounds having chemical structures of nucleic acid molecules, peptides, proteins, carbohydrates, lipids, inorganic protective compounds or other organic protective compounds.

Nucleic acid molecule compounds of the present invention can be DNA, RNA, or derivatives of either DNA or RNA and can include, but are not limited to, genes and portions thereof, including regulatory regions and/or coding regions, as well as oligonucleotides (typically less than about 60 to about 90 nucleotides) that can function as protective compounds such as antisense nucleic acid molecules, triplex-forming nucleic acid molecules, ribozymes and/or nucleic acid based-drugs. Nucleic acid based-drugs include, but are not limited to, drugs composed of natural or modified nucleic acids. Such drugs can be identified by selective screening of random samples of nucleic acid molecules with a binding partner for which a drug that can interact with such a binding partner is desired, using, for example, systematic evolution of ligands by exponential enrichment (SELEX) technology (see, for example, Tuerk et al., 1990, *Science* 249, 505–510). Nucleic acid molecule compounds can include nucleic acid molecules that encode one or more protective RNA (i.e., RNA transcripts of such nucleic acid molecules), peptide or protein compounds. Such nucleic acid molecules are transformed (i.e., inserted) into yeast vehicles in such a manner that they can be expressed into such protective RNA, peptide or protein compounds. Transformation of a nucleic acid molecule into a yeast cell can be accomplished by any method by which a nucleic acid molecule can be inserted into the cell. Transformation techniques include, but are not limited to, transfection, electroporation, microinjection, lipofection, adsorption, and protoplast fusion. Transformed nucleic acid molecules can be integrated into a yeast chromosome or maintained on extrachromosomal vectors using techniques known to those skilled in the art. Examples of yeast vehicles carrying such nucleic acid molecules are disclosed in detail herein.

As used herein, a peptide comprises an amino acid sequence of less than or equal to about 30 amino acids, while a protein comprises an amino acid sequence of more than about 30 amino acids; proteins can be multimeric. Peptides and proteins can be derivatized either naturally or synthetically; such modifications can include, but are not limited to, glycosylation, phosphorylation, acetylation, myristylation, prenylation, palmitoylation, amidation and/or addition of glycerophosphatidyl inositol. Peptides and proteins can be inserted directly into yeast vehicles of the present invention by techniques known to those skilled in the art, such as by electroporation, liposome fusion or bath sonication, or they can be produced by nucleic acid molecules transformed into yeast vehicles as disclosed herein. Peptides and proteins can be of a number of types, including, but not limited to, antibodies, enzymes, regulatory proteins and toxins.

Carbohydrate and lipid compounds of the present invention include, respectively, sugar and fatty acid groups. Inorganic protective compounds include compounds capable of protecting an animal from a disease that do not contain a carbon moiety; such compounds are also referred to herein as inorganic drugs, and include known (e.g., classic) as well as novel compounds. Organic protective compounds include those heretofore disclosed as well as other organic compounds, such as organic drugs that typically are synthesized microbially or synthetically. Such compounds include, but are not limited to, antibiotics, vitamins, steroids, anti-inflammatory compounds, antihistamines, anti-hypertensive agents, α and β adrenergic inhibitors and angiotensin converting enzyme (ACE) inhibitors.

It is within the scope of the present invention that yeast vehicles can be genetically engineered to produce carbohydrate, lipid or other organic protective compounds. Alternatively, such compounds, as well as inorganic protective compounds, can be loaded into yeast vehicles by, for example, diffusion or active transport. It is to be understood that loaded yeast vehicles include yeast vehicles that are loaded in the manner disclosed immediately above as well as those into which nucleic acid molecules, peptides and/or proteins are inserted using known techniques such as those disclosed above.

In accordance with the present invention, compounds included in yeast vehicles can have a variety of functions. Yeast vehicles of the present invention preferably include compounds capable of stimulating an immune response, compounds capable of suppressing an immune response, toxic compounds, compounds capable of inhibiting transcription of a gene, compounds capable of inhibiting translation of a gene, compounds capable of inhibiting the ability of an infectious agent to produce progeny, compounds capable of replacing a defective gene, compounds capable of replacing a defective protein (including nucleic acid molecules capable of encoding such proteins and mimetopes of such proteins) and/or biological response modifiers (e.g., cytokines, such as lymphokines and monokines, as well as other growth modulating factors), and mixtures thereof. Examples of such compounds include, but are not limited to, antibiotics, antibodies, antifungal compounds, antigens, antiparasite compounds, antisense compounds, antiviral compounds, chemotherapeutic agents, cytokines, growth modulating factors (including both growth stimulants and suppressants), herbicides, hormones, immunosuppressants, nucleic acid-based drugs (e.g., DNA- or RNA-based drugs), nucleic acid molecules comprising coding regions, nucleic acid molecules comprising regulatory sequences, nucleoside analogs, other oligonucleotides, peptide analogs, peptides, pesticides, prodrugs (e.g., compounds that are activated at the site of action), other proteins, ribozymes, steroids, toxins, and/or vitamins.

The present invention includes yeast vehicles that carry compounds that bind to other compounds and, as such, are referred to as binding partner compounds. Examples of binding partners include, but are not limited to, antigens and antibodies, class I and class II MHC molecules and their respective peptides, T cell receptors and their respective antigens, other receptors and their respective ligands, and nucleic acid molecules and regulatory proteins that bind to certain nucleic acid sequences on such molecules. Binding partner complexes, such as antigen-antibody complexes, consist of a first binding partner and a second binding partner; as used herein the number designation of the binding partner is irrelevant except for the limitation that a first binding partner must be able to bind to a second binding partner (e.g., it does not matter whether the antigen or antibody is labeled as the first binding partner, as long as the other compound is labeled as the second binding partner). In some complexes, additional partners are also included. Preferred first binding partners to include as compounds in yeast vehicles of the present invention include viral antigens, mammalian cell surface molecules, bacterial antigens, fungal antigens, protozoan antigens, helminth antigens, ectoparasite antigens, cancer antigens and/or proteins that bind to specific sites on DNA and/or RNA. Also preferred are second binding partners capable of binding to preferred first binding partners, nucleic acid molecules encoding preferred first or second binding partners and/or oligonucleotides capable of blocking production of preferred first or second binding partners (e.g., antisense, ribozyme and/or triplex formation complexes capable of inhibiting transcription and/or translation of the binding partner). Particularly preferred compounds to include in yeast vehicles of the present invention include viral antigens, cancer antigens, mammalian cell surface receptors and ligands of such receptors, as well as nucleic acid molecules that encode such compounds and/or oligonucleotides that block production of such compounds.

Examples of viral antigens to be used in yeast vehicles of the present invention include, but are not limited to, env, gag, rev, tar, tat, nucleocapsid proteins and reverse transcriptase from immunodeficiency viruses (e.g., HIV, FIV); HBV surface antigen and core antigen; HCV antigens; influenza nucleocapsid proteins; parainfluenza nucleocapsid proteins; human papilloma type 16 E6 and E7 proteins; Epstein-Barr virus LMP-1, LMP-2 and EBNA-2; herpes LAA and glycoprotein D; as well as similar proteins from other viruses.

Examples of cancer antigens to be used in yeast vehicles of the present invention include but are not limited to, MAGF, PSA, CEA, HER2/nev, MART1, BCR-abl, and mutant oncogenic forms of p53, ras, myc and RB-1.

Examples of mammalian cell surface molecules to be used in yeast vehicles of the present invention include MHC antigens, antibodies and T-cell receptors as well as other receptors and their ligands, such as Fas and Fas ligand, ICAM-1, LFA-1, NCAM, P-selectin and VCAM.

Other preferred antigenic compounds to include in yeast vehicles of the present invention include compounds that are antigens derived from suitable and preferred infectious agents as disclosed above as well as compounds that are linked to additional diseases as disclosed above, such as tumor antigens. Additional preferred compounds are compounds (including proteinaceous compounds) that are capable of suppressing an undesired, or harmful, immune response, such as is caused, for example, by allergens, autoimmune antigens, inflammatory agents, antigens involved in GVHD, certain cancers, septic shock antigens, and antigens involved in transplantation rejection. Such compounds include, but are not limited to, antihistamines, cyclosporin, corticosteroids, FK506, peptides corresponding to T cell receptors involved in the production of a harmful immune response, Fas ligands (i.e., compounds that bind to cellular Fas receptors, thereby inducing apoptosis), suitable MHC complexes presented in such a way as to effect tolerization or anergy, T cell receptors, and autoimmune antigens, preferably in combination with a biological response modifier capable of enhancing or suppressing cellular and/or humoral immunity. Also included as preferred compounds are nucleic acid molecules encoding any of the aforementioned compounds that are proteinaceous.

Particularly preferred yeast vehicles of the present invention are those that carry compounds that can modulate an immune response in an animal to which such vehicles are administered. As used herein, compounds that can modulate an immune response are compounds that, particularly when administered as part of a yeast vehicle, are able to regulate an immune response in order to stimulate a desired (i.e., protective) immune response or to suppress an immune response that is harmful (i.e., damaging, detrimental) to the organism. Modulation also includes the ability to switch between primarily cell-mediated and primarily humoral immune responses. Compounds that modulate an immune response can include inorganic or organic compounds and preferably include proteins and nucleic acid molecules encoding such proteins. Yeast vehicles are well suited to being used to modulate an immune response particularly in light of the discovery by the inventors that yeast vehicles of the present invention are able to stimulate cell-mediated as well as humoral immunity. While it is as yet unknown why antigenic compounds carried by yeast vehicles are processed through the class I MHC-based pathway, the identification of yeast vehicles as being able to stimulate cell-mediated immunity is quite advantageous.

A particularly preferred embodiment of the present invention is the use of yeast vehicles to protect an organism against infection, and particularly against viral infection. Preferred compounds to include in such yeast vehicles are viral antigens such as viral surface proteins and/or viral core proteins (including structural and nonstructural proteins), and/or nucleic acid molecules encoding such antigens and/or oligonucleotides capable of blocking production of such antigens. Particularly preferred viral antigens (or nucleic acid molecules corresponding thereto) include those of immunodeficiency and/or tumor viruses, and more preferably those of HIV (e.g., HIV-1 or HIV-2), HTLV (e.g., HTLV-I or HTLV-II), FIV or FLV.

Yeast vehicles of the present invention can also include biological response modifier compounds, or the ability to produce such modifiers (i.e., by carrying genes encoding such modifiers). Preferred are yeast vehicles that include at least one antigen and at least one biological response modifier compound. Biological response modifiers are compounds that can modulate immune responses. Certain biological response modifiers can stimulate a protective immune response whereas others can suppress a harmful immune response. Certain biological response modifiers preferentially enhance a cell-mediated immune response whereas others preferentially enhance a humoral immune response (i.e., can stimulate an immune response in which there is an increased level of cellular compared to humoral immunity, or vice versa.). There are a number of techniques known to those skilled in the art to measure stimulation or suppression of immune responses, as well as to differentiate cellular immune responses from humoral immune responses.

Suitable biological response modifiers include cytokines and other growth modulators, such as, but not limited to, interleukin 2 (IL-2), interleukin 4 (IL-4), interleukin 10 (IL-10), interleukin 12 (IL-12), interferon gamma (IFN-gamma) insulin-like growth factor I (IGF-I), and/or transforming growth factor beta (TGF-$\beta$). The ability of a yeast vehicle to express (i.e., produce), and preferably secrete, IL-2, IL-12 and/or IFN-gamma preferentially enhances cell-mediated immunity, whereas the ability of a yeast vehicle to express, and preferably secrete, IL-4, IL-5 and/or IL-10 preferentially enhances humoral immunity.

One advantage of the present invention is that yeast vehicles of the present invention can target desired cell types, thereby delivering compounds essentially only to a selected subset of all cell types. That is, the yeast vehicles can deliver their compounds to a desired cell type, but essentially not to other cell types, based, for example, on the ability of the yeast vehicle to recognize cell surface molecules that are present on the desired cell type (i.e., targeted cell type) but are essentially not absent from other cell types (i.e., non-targeted cell types). That is, the yeast vehicle is capable of selectively recognizing the selected cell type. In one embodiment, the inherent ability of yeast cells to be adsorbed by certain cell types is relied upon to deliver compounds carried by yeast vehicles of the present invention to such cell types. As used herein, the term adsorb refers to the ability of a given cell type to take up yeast vehicles of the present invention by, for example endocytosis or phagocytosis. In another embodiment, yeast vehicles are genetically engineered to target compounds to a variety of additional cell types.

One embodiment of the present invention is a method to deliver a compound to a given (i.e., desired or selected) cell type by administering to a population of cells including that cell type a composition including a yeast vehicle of the present invention that is capable of targeting the compound to that cell type. A population of cells can refer to cells, tissues or organs in culture, in which case the composition is administered in vitro. A population of cells can also refer to an organism, preferably to an animal or to a plant, in which case the composition is administered in vivo and/or ex vivo.

As used herein a cell type refers to a class of cells (e.g., lymphocytes, muscle cells, epithelial cells, etc.) and can include single cells, cell aggregates, tissues and organs. The compound, which is carried by the yeast portion of the vehicle, is heterologous to the yeast portion. A number of suitable and preferred compounds are heretofore disclosed.

Unless engineered to do otherwise, yeast vehicles of the present invention can deliver compounds to cell types that naturally adsorb yeast. Cell types naturally targeted by yeast include, but are not limited to, cells of granulocytic-monocytic lineage, B lymphocytes and T lymphocytes. Examples of cells of granulocytic-monocytic lineage include, but are not limited to, dendritic cells, histiocytes, Kupffer cells, Langerhans cells, other macrophages (including alveolar and spleen free and fixed macrophages), microglia, neutrophils, osteoclasts, and reticulo-endothelial cells. These yeast vehicles are particularly preferred for the stimulation of mucosal immunity as these vehicles are capable of targeting cells located in the epithelial regions of an animal. As such, these yeast vehicles are particularly suitable to protect animals from diseases that affect epithelial tissues, such as viral infections and epithelial cancers, including, but not limited to cervical, colon and certain lung cancers.

Additional yeast vehicles of the present invention are engineered to deliver compounds to one or more cell types. Such yeast vehicles include a heterologous component positioned on the yeast vehicle's outer membrane (i.e., entirely on the yeast vehicle's outer membrane or at least partially embedded within the membrane) in such a manner that the component is capable of targeting (i.e., selectively delivering) the yeast vehicle to the given cell type(s). Such components are of a species or type that is different from the species, or subspecies, of yeast used in the production of the vehicle. A preferred heterologous component is a binding partner of an element (such as a receptor, antigen, or other cell surface entity), positioned on the surface of the given cell type that is being targeted for delivery. Such an element is preferably absent from, or found in only in small amounts, on cell types that are not targeted for delivery.

Preferred cell types to target using heterologous component-containing yeast vehicles of the present invention include connective tissue cells, dendritic cells, endothelial cells, epithelial cells, cells of granulocytic-monocytic origin, hematopoietic stem cells, hepatocytes, lymphocytes, myoblasts, myocytes, neurons, neutrophils, pneumocytes, thymocytes, and combinations thereof. Preferred epithelial cells to target include genital, intestinal, kidney, mucosal, and pulmonary epithelial cells. Preferred lymphocytes to target include B lymphocytes and T lymphocytes. Particularly preferred cell types to target include cells that express CD4 or CD8 cell markers on their cell surfaces, with cells expressing CD4 being even more preferred. Cells having CD4 cell markers include helper T cells, macrophages and reticuloendothelial cells; cells having CD8 cell markers include cytotoxic T cells.

Heterologous components suitable for including in yeast vehicles of the present invention include, but are not limited to, antibodies that selectively bind to elements found on the surface of certain cell types, asialoglycoproteins (glycoproteins lacking sialic acid groups), complement C3d proteins, Fas ligands, fusogens, T cell receptors, other receptors, receptor ligands (e.g., antigens, cytokines and growth factors), transferring, viral surface proteins (e.g., viral proteins that enable viruses to infect their respective host cells), other cell surface proteins, and mixtures thereof. Preferred heterologous components include antibodies, Fas ligands, receptor ligands, and viral surface proteins, with Fas ligands and viral surface proteins being particularly preferred.

In a preferred embodiment, a yeast vehicle having a heterologous component which targets a selected cell type is capable of producing (i.e., expressing) that component and of positioning the component on the vehicle's outer membrane in a manner suitable to target the vehicle to a desired cell type. Such a yeast vehicle is a vehicle that is transformed with a nucleic acid molecule encoding the component. The nucleic acid molecule is situated in the yeast vehicle in such a manner that the component can be expressed by the yeast vehicle; e.g., the nucleic acid molecule is operatively linked (i.e., joined) to a transcription control sequence. Methods to express heterologous nucleic acid molecules in yeast vehicles are disclosed herein.

A preferred yeast vehicle of the present invention is capable of fusing with the cell type to which a compound carried by the vehicle is being delivered, thereby effecting particularly efficient delivery of the compound to the cell type. Such a yeast vehicle includes a heterologous component capable of effecting fusion with the cell membrane of the targeted cell type. As used herein, fusion of a yeast vehicle with a targeted cell type refers to the ability of the yeast cell membrane to fuse with the membrane of the targeted cell type, leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). For example, a yeast vehicle that produces an HIV gp120/gp41 heterologous component on its surface is capable of fusing with a CD4+ T-lymphocyte. It is within the scope of the present invention to increase the number of heterologous components that can be used in the production of yeast vehicles capable of fusing with a given cell type by producing a complex between a heterologous component that by itself cannot fuse and a component capable of inducing fusion, such as by hooking transferrin to the HIV gp41 protein.

In one embodiment, a yeast strain is genetically engineered to target cells naturally targeted by other yeast strains or to make vaccines against certain pathogenic yeast strains. For example, nucleic acid molecules encoding Candida or Chlamydia antigens can be genetically engineered into a *S. cerevisiae* strain such that the Candida or Chlamydia antigens are expressed and incorporated into the *S. cerevisiae* membrane. The resultant yeast vehicle when administered to an animal is capable of stimulating a protective immune response, including a cell-mediated as well as a humoral immune response, against, respectively, Candida or Chlamydia infection.

Yeast vehicles of the present invention can be produced using methods known to those skilled in the art. Yeast vehicles can be loaded with compounds using a variety of techniques suitable for the compound(s) being loaded. For example, as heretofore disclosed, inorganic compounds and a number of organic compounds can be inserted into yeast vehicles by diffusion and/or active transport. Peptides and proteins can be loaded into yeast vehicles by liposome fusion, electroporation or bath sonication.

Preferred yeast vehicles of the present invention are genetically engineered (i.e., recombinantly produced) yeast vehicles. Such vehicles are transformed with one or more nucleic acid molecules capable of encoding RNA, peptide or protein compounds of the present invention. Yeast vehicles can also be transformed with nucleic acid molecules encoding enzymes and/or other factors thereby enabling such vehicles to produce other compounds of the present invention (e.g., antibiotics or vitamins). Certain yeast vehicles of the present invention are transformed with a nucleic acid molecule encoding a compound to be delivered to a given organism and with a nucleic acid molecule encoding a heterologous component capable of targeting the vehicle to a given cell type. In one embodiment, the compound and heterologous component are the same protein (e.g., a viral surface antigen vaccine targeted to a cell type susceptible to infection by such a virus).

Transformation of yeast portions of a yeast vehicle can be accomplished using known techniques, examples of which are disclosed herein. Yeast vehicles capable of producing compounds and heterologous components include, but are not limited to, intact yeast microorganisms and yeast spheroplasts. Yeast cytoplast, yeast ghost, and yeast membrane particle vehicles can also be produced recombinantly by transforming intact yeast microorganisms or yeast spheroplasts with desired nucleic acid molecules, producing RNA, peptide or protein compounds therein, and further manipulating the microorganisms or spheroplasts using techniques known to those skilled in the art to produce cytoplast, ghost or membrane particle vehicles containing desired compounds.

In one embodiment, membrane particle vehicles are produced by culturing an intact yeast microorganism or spheroplast transformed with a nucleic acid molecule that can be expressed by the yeast microorganism or spheroplast into a protein that can be transported to the membrane of the yeast microorganism or spheroplast. Such production strains are then submitted to known techniques to isolate yeast membranes that include the desired compounds. Examples of such compounds include viral surface proteins and other proteins that normally are found on a membrane surface. Yeast membrane particles are particularly useful in modulating an immune response.

Nucleic acid molecules transformed into yeast vehicles of the present invention can include one or more genes, or portions thereof. Such nucleic acid molecules can comprise partial or entire coding regions, regulatory regions, or combinations thereof as well as regions that when transcribed are capable of interfering with protein production. One advantage of yeast strains is their ability to carry a number of nucleic acid molecules and of being capable of producing a number of heterologous RNA and/or protein compounds. As such, yeast vehicles of the present invention can be designed to protect an animal from more than one disease or to carry more than one compound for other uses. A preferred number of compounds to be produced by a yeast vehicle of the present invention ranges from about one to about 5, with from about 2 to about 5 compounds being more preferred. Particularly preferred is a yeast vehicle including the following gene classes: a gene encoding a vaccine, a gene encoding a biological response modifier, and a gene encoding a heterologous component suitable for targeting a desired cell type.

A peptide or protein encoded by a nucleic acid molecule within a yeast vehicle can be a full-length protein, or can be a functionally equivalent protein in which amino acids have been deleted (e.g., a truncated version of the protein), inserted, inverted, substituted and/or derivatized (e.g., acetylated, glycosylated, phosphorylated, tethered by a glycerophosphatidyl inositol (GPI) anchor) such that the modified protein has a biological function substantially similar to that of the natural protein. Modifications can be accomplished by techniques known in the art including, but not limited to, direct modifications to the protein or modifications to the gene encoding the protein using, for example, classic or recombinant DNA techniques to effect random or targeted mutagenesis. Functionally equivalent proteins can be selected using assays set up to measure the biological activity of the protein.

Expression of an RNA, peptide or protein compound in a yeast vehicle of the present invention is accomplished using techniques known to those skilled in the art. Briefly, a nucleic acid molecule encoding a desired compound is inserted into an expression vector in such a manner that the nucleic acid molecule is operatively joined to a transcription control sequence in order to be capable of effecting either constitutive or regulated expression of the nucleic acid molecule when transformed into a host yeast cell. Nucleic acid molecules encoding one or more compounds can be on one or more expression vectors operatively linked to one or more transcription control sequences.

A recombinant molecule herein refers to a nucleic acid molecule operatively linked to at least one transcription control sequence on an expression vector. An expression vector herein refers to a DNA or RNA vector that is capable of transforming a host cell and of effecting expression of the operatively linked nucleic acid molecule. Such vectors also preferably can replicate within the host cell, to either a high or low copy number depending on their inherent characteristics.

Transcription control sequences, which can control the amount of protein produced, include sequences which control the initiation, elongation, and termination of transcription. Particularly important transcription control sequences are those which control transcription initiation, such as promoter and upstream activation sequences. Any suitable yeast promoter can be used in the present invention and a variety of such promoters are known to those skilled in the art. Preferred promoters for expression in *Saccharomyces cerevisiae* include, but are not limited to, promoters of genes encoding the following yeast proteins: alcohol dehydrogenase I (ADH1) or II (ADH2), phosphoglycerate kinase (PGK), triose phosphate isomerase (TPI), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome $c_1$ (CYC1) and acid phosphatase (PHO5), with hybrid promoters such as ADH2/GAPDH and CYC1/GAL10 promoters being more preferred, and the ADH2/GAPDH promoter, which is induced when glucose concentrations in the cell are low (e.g., about 0.1 to about 0.2 percent), being even more preferred. Likewise, a number of upstream activation sequences (UASs), also referred to as enhancers, are known. Preferred upstream activation sequences for expression in *Saccharomyces cerevisiae* include, but are not limited to, the UASs of genes encoding the following proteins: CYC1, ADH2, GAL1, GAL7 and GAL10, as well as other UASs activated by the GAL4 gene product, with the ADH2 UAS being particularly preferred. Since the ADH2 UAS is activated by the ADR1 gene product, it is preferable to overexpress the ADR1 gene when a heterologous gene is operatively linked to the ADH2 UAS. Preferred transcription termination sequences for expression in *Saccharomyces cerevisiae* include the termination sequences of the α-factor, GAPDH, and CYC1 genes.

Preferred transcription control sequences to express genes in methyltrophic yeast include the transcription control regions of the genes encoding alcohol oxidase and formate dehydrogenase.

Nucleic acid molecules used in the present invention can also include endogenous or heterologous secretion sequences as well as transmembrane anchoring sequences, as appropriate. For example, it is preferred to secrete biological response modifier compounds, whereas it is preferred to anchor heterologous components in the yeast vehicle membrane. The selection and use of such sequences can be accomplished using techniques known to those skilled in the art.

Effective conditions for the production of recombinant yeast vehicles of the present invention include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, test tubes, microtiter dishes, and petri plates. Culturing is carried out at a temperature, pH and oxygen content appropriate for the yeast strain. Such culturing conditions are well within the expertise of one of ordinary skill in the art (see, for example, Guthrie et al. (eds.), 1991, *Methods in Enzymology*, vol. 194, Academic Press, San Diego).

Yeast vehicles can be recovered by techniques known to those skilled in the art, including methods disclosed herein. Yeast vehicles can be formulated into compositions of the present invention using a number of techniques known to those skilled in the art. For example, yeast vehicle-containing compositions can be dried by lyophilization or by exposure to liquid nitrogen or dry ice. Compositions comprising yeast vehicles can also be prepared by packing yeast in a cake or a tablet, such as is done for yeast used in baking or brewing operations.

In order to administer a yeast vehicle to an organism, dried compositions can be used for oral delivery. Yeast vehicles can also be mixed with a pharmaceutically acceptable excipient, such as an isotonic buffer that is tolerated by the organism to be administered the vehicle. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

One particular advantage of the present invention is that yeast vehicles do not need to be administrated with an immunopotentiator such as an adjuvant or a carrier, since the yeast portion of the vehicle itself appears to function as such. This characteristic, however, does not preclude the use of immunopotentiators in compositions of the present invention. As such, in one embodiment, a composition of the present invention can include one or more yeast vehicles and one or more adjuvants and/or carriers.

Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (CytRx™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark).

Carriers are typically compounds that increase the half-life of a therapeutic composition in the treated animal. Suitable carriers include, but are not limited to, polymeric controlled release formulations, biodegradable implants, liposomes, oils, esters, and glycols.

The present invention includes the delivery of a composition comprising a yeast vehicle of the present invention to an animal or to cells in culture. Such compositions can be delivered to an animal either in vivo or ex vivo, or can be delivered to cells in vitro. As used herein, in vivo delivery refers to the administration of a composition comprising a yeast vehicle directly to an animal. Such administration can be systemic, mucosal and/or proximal to the location of the targeted cell type. Examples of routes to administer a yeast vehicle in vivo include aural, bronchial, genital, inhalatory, nasal, ocular, oral, parenteral, rectal, topical, transdermal and urethral routes. Aural delivery can include ear drops, nasal delivery can include nose drops and ocular delivery can include eye drops. Oral delivery can include solids and liquids that can be taken through the mouth. Parenteral delivery can include intradermal, intramuscular, intraperitoneal, intrapleural, intrapulmonary, intravenous, subcutaneous, atrial catheter and venal catheter routes. Oral delivery is preferred, particularly since oral delivery is useful in the development of mucosal immunity and since compositions comprising yeast vehicles can be easily prepared for oral delivery, for example, as tablets or capsules, as well as being formulated into food and beverage products. Other routes of administration that modulate mucosal immunity are also preferred, particularly in the treatment of viral infections, epithelial cancers, immunosuppressive disorders and other diseases affecting the epithelial region. Such routes include bronchial, intradermal, intramuscular, nasal, other inhalatory, rectal, subcutaneous, topical, transdermal, vaginal and urethral routes.

Ex vivo delivery of a yeast vehicle refers to a method that includes the steps of contacting a population of cells removed from an animal with a composition comprising a yeast vehicle of the present invention under conditions such that the yeast vehicle is adsorbed by targeted cell types and returning the contacted cells to the animal. Such a delivery method is particularly useful in the treatment of cells involved in hematopoiesis and the immune response as well as in the treatment of tumors.

In vitro delivery of a yeast vehicle refers to the delivery of a yeast vehicle of the present invention to a population of cells (which can also include tissues or organs) in culture. Such a method is particularly useful in determining whether a specific yeast vehicle will be efficacious in vivo or ex vivo and in research projects. Cells that are treated in vitro can be maintained in culture or transferred to an animal.

Methods to prepare and administer compositions via these routes are well known to those skilled in the art. Compositions of the present invention are administered in an effective manner which depends on the use of the composition. For example, in order to protect an animal from disease, a composition of the present invention is administered to the animal in an effective manner such that the composition is capable of protecting that animal from that disease. Compositions of the present invention can be administered to animals or plants prior to disease in order to prevent disease and/or can be administered to animals after onset of the disease in order to treat the disease. For example, yeast vehicles of the present invention can be used as preventative agents (prophylactics) and/or as immunotherapeutic agents.

Acceptable protocols to administer compositions in an effective manner include individual dose size, number of doses, frequency of dose administration, and mode of administration. Determination of such protocols can be accomplished by those skilled in the art. A suitable single dose is a dose that is capable of effectively delivering a compound being carried by the yeast vehicle to a given cell type when administered one or more times over a suitable time period. For example, a preferred single dose of a yeast vehicle of the present invention is from about $1 \times 10^5$ to about $5 \times 10^7$ yeast cell equivalents per kilogram body weight of the organism being administered the composition. "Boosters" of a yeast vehicle composition are preferably administered when the compound carried by the yeast vehicle is no longer functioning effectively. For example, if an immune response of an organism is no longer being effectively modulated, one or more additional doses of a composition of the present invention capable of modulating the desired immune response can be administered. Such compositions can be administered from about 2 weeks to several years after the original administration. A preferred administration schedule is one in which from about $1 \times 10^5$ to about $5 \times 10^7$ yeast cell equivalents of a composition per kg body weight of the organism is administered from about one to about 4 times over a time period of from about 1 month to about 6 months. Examples of methods to administer yeast vehicles of the present invention to animals are provided in the Examples section.

One embodiment of the present invention is a method to transfer a nucleic acid molecule into a given cell type. Such a method includes the step of administering to a population of cells including said cell type a composition that includes a yeast vehicle transformed with the nucleic acid molecule. The yeast vehicle is preferably capable of fusing with the cell type, thereby transferring (i.e., delivering) the nucleic acid molecule into that cell type. Such transfer can be accomplished in vitro if the population of cells is maintained in culture or in vivo and/or ex vivo if the population of cells comprise an organism, such as an animal or a plant.

In a preferred embodiment, the transfer of the nucleic acid molecule effects gene therapy. That is the nucleic acid molecule is capable of correcting a genetic defect. A composition that is able to effect gene therapy includes a yeast vehicle that is genetically engineered to effect stable gene therapy in the targeted cell type by, for example, being able to effect integration of the gene into the host genome, maintaining the fused cell as a heterokaryon, or using other mechanisms to stably maintain the gene in the treated cell type. Such a composition is administered to an organism in vivo or ex vivo using techniques such as those developed for other gene delivery vehicles. Yeast delivery vehicles are advantageous because they can form syncytia with the cells to which they are transferring the desired gene to effect gene therapy and can be targeted to particular cell types, as disclosed herein. For example, a genetic defect that leads to cystic fibrosis may be corrected using a yeast vehicle carrying a functional CFTR (cystic fibrosis transmembrane conductance regulator) gene that is targeted to terminally differentiated cells positioned proximal to the outer layer of the lung. It is also to be noted that genes encoding proteins that are secreted into bodily fluids need not be targeted to a specific cell type.

Yeast vehicle compositions of the present invention can be administered to any suitable animal, including any animal susceptible to any disease from which a yeast vehicle of the present invention can be designed to protect the animal. Preferred animals to treat include vertebrates and arthropods, with mammals, amphibians, bird, fish and insects being more preferred. Even more preferred animals to treat include humans, primates, companion animals (i.e., pets) and agriculturally important animals (i.e., livestock), with humans, apes, cats, cattle, dogs, ferrets, gorillas, horses, mice, monkeys, pigs, rabbits, rats and sheep being particularly preferred.

Yeast vehicles of the present invention can also be administered to plants, preferably to angiosperms and more preferably to agricultural crops by, for example, exposing seeds or germ to yeast vehicle-containing compositions, or by fusing yeast vehicles with Agrobacterium. Examples of agricultural crops include plants raised for their flowers, fruits, vegetables or seeds, such as apples, barley, beans, carrots, cherries, corn, grapes, legumes, oranges and other citrus fruits, peaches, soybeans, tomatoes and wheat. In one embodiment, yeast vehicles of the present invention are administered to plants to treat infections by, for example, viroids, viruses, or other pathogenic agents or to administer herbicides or pesticides. For example, a yeast vehicle of the present invention can be administered to grapes to protect grapes against phyloxera.

The present invention includes a variety of novel compositions that include yeast vehicles of the present invention. One composition includes (a) a yeast vehicle having (i.e., including) at least one compound that is heterologous to the yeast vehicle and (b) a pharmaceutically acceptable excipient. Such a composition can be used in the delivery of the compound to an organism or to cells in culture using methods disclosed herein. Such a composition is novel since yeast strains carrying heterologous compounds have not, to the inventors' knowledge, been combined with excipients. Furthermore, such a composition is not obvious since until the present invention there was no appreciation in the art to use yeast as delivery vehicles. Suitable compounds, yeast vehicles and excipients are disclosed herein. Examples of yeast vehicles include, but are not limited to, gene delivery vehicles (i.e., yeast vehicles carrying nucleic acid molecules to effect gene therapy), drug delivery vehicles (i.e., yeast vehicles carrying inorganic or small organic compounds, such as, but not limited to, antibiotics, steroids, other classic drugs, RNA-based drugs), and immunomodulatory yeast vehicles (i.e., yeast vehicles that carry any of a variety of compounds disclosed herein that are capable of modulating an immune response).

Another composition of the present invention includes a yeast vehicle having (i.e., including) (a) a heterologous component positioned on the yeast vehicle's outer membrane in such a manner that the component is capable of targeting the yeast vehicle to a given cell type and (b) a heterologous compound. Suitable heterologous components and heterologous compounds are disclosed herein. Such yeast vehicles can include more than one heterologous component and/or more than one heterologous compound. Such compositions can also include other members, including, but not limited to, an excipient, adjuvant, and/or carrier, examples of which are disclosed herein.

Preferably, the heterologous component(s) and heterologous compound(s) are each produced by the yeast vehicle. Such a yeast vehicle is transformed with nucleic acid molecule(s) encoding a heterologous component and a heterologous compound in such a manner that the yeast is able to express the heterologous component and heterologous compound (which may be an RNA or protein compound). Another preferred yeast vehicle is a yeast vehicle capable of expressing a heterologous component and that is also carrying a nucleic acid molecule capable of effecting gene therapy (i.e., a gene delivery vehicle).

Another embodiment of the present invention is a composition including a yeast vehicle carrying at least two heterologous compounds capable of protecting an animal from a disease. Suitable compounds are disclosed herein. Such compositions can also include other members such as excipients, adjuvants and carriers. Yeast vehicles can also include heterologous components capable of targeting the vehicles to certain cell types. Yeast vehicles included in this embodiment include transformed yeast vehicles that are capable of producing one or more of the heterologous compounds.

Preferably at least one of the heterologous compounds is a compound capable of modulating an immune response, such as a compound capable of stimulating an immune response or a compound capable of suppressing an immune response. One preferred embodiment is a yeast vehicle carrying an antigen and a biological response modifier.

Another preferred embodiment is a yeast vehicle carrying an antigen, a biological response modifier and a heterologous component capable of targeting the yeast vehicle to a given cell type.

One embodiment of the present invention is a yeast vehicle comprising a yeast strain capable of producing a heterologous precursor protein having a dibasic amino acid processing site, wherein the yeast strain is capable of correctly processing the precursor protein into at least one cleavage protein. Examples of such precursor proteins include a number of hormone precursor proteins and viral envelope protein precursor proteins that require cleavage by a dibasic amino acid endoprotease as one step in the process of maturation. Examples of such precursor proteins (including, but not limited to, precursor proteins of immunodeficiency viruses, lymphotrophic viruses, hepatitis viruses and herpes viruses) are provided in U.S. patent application Ser. No. 08/088,322, ibid., and, as such, are incorporated herein.

Yeast produce a protein called Kex2 endoprotease that was shown in U.S. patent application Ser. No. 08/088,322, ibid., to be able to effect cleavage of heterologous precursor proteins having a dibasic amino acid processing site. As such, a yeast strain capable of expressing a viral envelope precursor protein can effect cleavage of such a precursor protein and express the mature envelope protein(s) on the yeast membrane. Yeast vehicles of the present invention capable of producing a heterologous precursor protein can also be genetically engineered to produce a heterologous Kex2-like endoprotease, such as the protease that naturally cleaves the heterologous precursor protein. Such yeast vehicles can, but need not be, engineered to no longer produce a functional yeast Kex2-endoprotease. Details regarding the production of such yeast vehicles are disclosed in U.S. patent application Ser. No. 08/088,322, ibid. Used in accordance with the present invention, such yeast vehicles can stimulate an immune response against infectious agents.

One example of the ability of a yeast vehicle of the present invention to elicit an immune response is as follows. A yeast vehicle transformed with a viral surface precursor protein, such as with HIV gp160, when administered to an animal, elicits both cell-mediated and humoral responses against HIV envelope proteins without having to include an adjuvant. Both T cell proliferative responses (indicative of helper T cell priming) and potent CD8+ cytotoxic T cell activity (indicative of cell-mediated immunity) are observed, supporting the concept that yeast vehicles are capable of leading to presentation of antigens through both class I and class II MHC pathways. Particularly preferred yeast vehicles to use to protect an animal against HIV infection include AFY435-gp160-SF2(c), an intact $S.$ $cerevisiae$ cell engineered to express the gp160 precursor envelope protein of HIV-$1_{SF}2$ and AFY435-gp160-SF2(s), a spheroplast otherwise equivalent to AFY435-gp160-SF2(c). Details of such embodiments are disclosed in the Examples section.

Another embodiment of the present invention is a yeast vehicle that is capable of stimulating an immune response to kill cancer cells. Such a yeast vehicle contains (and preferably expresses) proteins, or peptides thereof, that are found substantially only on or in cancer cells, including proteins that cause cancer because they have mutated (e.g., ras) When administered to an animal, such a yeast vehicle induces an immune response that includes the production of cytotoxic T cells capable of killing cells that express proteins corresponding to the proteins or peptides thereof carried by the yeast vehicle, i.e., cancer cells.

Certain yeast vehicles of the present invention are particularly useful in suppressing, or reducing, harmful immune responses. In one embodiment, a yeast vehicle of the present invention expresses on its membrane surface appropriate peptides corresponding to T cell receptors present on cells involved in the production of a harmful immune response in an animal. Administration of such a yeast vehicle to the animal results in the production of cytotoxic T cells targeted against cells expressing the T cell receptors, thereby suppressing immune responses generated by such cells. Methods to identify appropriate peptides and the use of other delivery vehicles to effect such a response are disclosed in, for example, Bourdette et al., 1994, *J. Immunol.* 152, 2510–2519 and Chou et al., 1994, *J. Immunol.* 152, 2520–2529. Yeast vehicles are particularly useful for such an approach due to their ability to generate a strong cell-mediated response as well as a humoral response. A similar approach can be taken to reduce harmful or ineffectual immune responses induced by parasites, tumors or viruses in order to trick the immune system of the diseased individual; i.e., by using a yeast vehicle capable of inducing a cytotoxic T cell response against T cells or B cells involved in the production of harmful and/or nonprotective antibodies.

In another embodiment, a yeast vehicle of the present invention expresses on its cell membrane a Fas ligand and, as such, is able to kill cells expressing a molecule called Fas (CD95). Fas is a glycoprotein that is found on certain cell types, including activated T lymphocytes and cancer cells, including leukemia and lymphoma cells; see, for example, Suda et al., 1993, *Cell* 75, 1169–1178. Use of yeast as a delivery vehicle for Fas ligands in order to kill targeted cell types is advantageous since, for example, the Fas ligands can be presented in a manner similar to how they are presented naturally, which is apparently aggregated on a cell membrane, such as on a cytotoxic T cell.

Another embodiment of the present invention is a yeast vehicle expressing major histocompatibility complex (MHC) molecules on its cell membrane. It is within the scope of the present invention to have yeast vehicles carrying empty MHC molecules which can be loaded in vitro, as well as MHC molecules complexed to peptides, using, for example, techniques similar to those used for expressing empty and complexed MHC molecules in baculovirus; see, for example, Stern et al., 1992, *Cell* 68, 465–477. Such yeast vehicles can be used to modulate immune responses, such as to delete or inactivate T cells involved in autoimmune and other harmful immune responses.

The present invention also includes a method to test the ability of a yeast vehicle of the present invention to protect an animal from a disease using a surrogate animal model in which a yeast vehicle can be tested. Preferred surrogate animals include rodents and primates. In one embodiment, the method can determine the ability of a yeast vehicle to elicit an immune response in a relatively inexpensive laboratory animal, such as a rodent (e.g., a mouse, rat, guinea pig, gerbil, rabbit) even though the animal is not susceptible to the disease against which the yeast vehicle is designed to protect (i.e., an animal in which disease symptoms do not normally develop). Using this method, for example, an animal can be tested to determine whether a yeast vehicle that expresses HIV gp160 is capable of inducing that animal to produce T cells that are capable of killing gp160-transfected cells.

As such, the present invention includes a method to test in a model comprising a surrogate animal the ability of a yeast vehicle of the present invention to elicit a protective immune response against a disease. The method includes the steps of (a) treating the surrogate animal with a composition including a yeast vehicle transformed with a heterologous nucleic acid molecule that expresses a compound being tested for the ability to elicit a protective immune response, thereby producing a treated animal (i.e., an animal having been administered the composition); (b) administering to the treated animal a tumor cell transformed with the same heterologous nucleic acid molecule, wherein the tumor cell is lethal to an untreated animal (i.e., an animal of the same species as the treated animal); and (c) determining if the treated animal survives the step of treating (i.e., survives in spite of administrating of the tumor cell(s)). Survival of the treated animal indicates that the yeast vehicle being tested is capable of eliciting a protective immune response against that disease. In accordance with this method, the genetically-engineered tumor cells are functioning as surrogate targets. In the case of HIV, for example, the tumor cells are functioning as surrogates for HIV-infected T cells, which are the targets in humans for yeast vehicles of the present invention that can stimulate a cell-mediated as well as a humoral response against HIV. As used herein, the phrase "a tumor cell" refers to one or more tumor cells and can refer to a solid tumor.

In a particularly preferred embodiment, the method includes a step of treating an animal with a yeast vehicle that can express HIV gp160. Subsequently, tumor cells which have been engineered to produce HIV gp160 (e.g., tumor cells transformed with an HIV gp160 gene in a manner that permits expression of that gene) and which, upon administration into naive (untreated) animals, lead to the growth of tumors in the animals that can be lethal (e.g., fibrosarcoma cells or melanoma cells for mice), are introduced into the animals that were treated with the yeast vehicle. Finding that growth of tumor cells in such animals is inhibited indicates that the yeast vehicle stimulated an immune response capable of killing cells that expressed the compound of interest (in this case, tumor cells expressing gp160 and/or processed gp120/gp41).

The following experimental results are provided for purposes of illustration and are not intended to limit the scope of the invention.

EXAMPLES

Molecular and cell biology techniques used in the following examples are known to those skilled in the art and are described, for example, in Sambrook et al., *Molecular Cloning: A Laboratory Manual*, Cold Spring Harbor Labs Press, 1989; and Guthrie et al. (eds.), ibid.

Example 1

This Example describes the production of certain yeast vehicles of the present invention.

*S. cerevisiae* AFY435-gp160-SF2, also denoted *S. cerevisiae* GPY60:pα/env, was produced as described in Example 1 of U.S. patent application Ser. No. 08/088,322, ibid. Briefly, the envelope (env) gene encoding the gp160 precursor envelope protein (about 825 amino acids) of HIV-$1_{SF2}$ (Sanchez-Pescador et al., 1985, *Science* 227, 484–492) was ligated to a nucleic acid sequence encoding an α-factor signal and leader segment of about 86 amino acids to form an α-leader/env-gene fragment (α/env) in which the signal sequence of the env gene was replaced by the α-factor signal and leader sequences in a manner similar to the method by which the epidermal growth factor gene was joined to α-factor signal and leader sequences in Brake et al., 1984, *Proc. Natl. Acad. Sci.* 81, 4642–4646. The α-factor segment, also denoted α-F leader, also included a dibasic amino acid processing site at its carboxyl terminus. The α/env fusion gene was operatively linked to a *S. cerevisiae* ADH2/GAPDH promoter and α-factor transcription termination sequences and joined with other yeast shuttle expression vector sequences to form recombinant molecule pα/env, also denoted pBS8. Recombinant molecule pα/env contains yeast (2μ) and bacterial replication control sequences as well as a bacterial gene encoding ampicillin resistance (Amp), and auxotrophic leu2-d and prototrophic URA3 yeast genes.

Recombinant molecule pα/env was transformed into several *S. cerevisiae* strains, including GPY60, a Matα pep4::URA3 prb leu2 his4 ura3 trp1 strain which is described in Baker et al., 1988, *Cell* 54, 335–344. The transformed strain is denoted *S. cerevisiae* GPY60:pα/env, or *S. cerevisiae* AFY435-gp160-SF2. A yeast vehicle comprising the intact yeast cell AFY435-gp160-SF2 was denoted AFY435-gp160-SF2(c). A yeast vehicle comprising a spheroplast of AFY435-gp160-SF2 was denoted AFY435-gp160-SF2(s).

Example 1 of U.S. patent application Ser. No. 08/088,322, ibid., also demonstrates (a) that *S. cerevisiae* AFY435-gp160-SF2 produced HIV-1 gp160 precursor envelope protein and was able to process gp160 into gp120 and gp41 in vivo in a manner similar to that by which mammalian cells process gp160, and (b) that *S. cerevisiae* AFY435-gp160-SF2 expressed at least a portion of the cleaved gp120 and gp41 proteins on its cell surface.

Example 2

This example demonstrates that yeast vehicles of the present invention are capable of stimulating cell-mediated as well as humoral immune responses in animals.

A. Yeast vehicles

Intact cell and spheroplast *S. cerevisiae* yeast vehicles engineered to express the gp160 precursor envelope protein of HIV-1$_{SF2}$ were tested in mice for their ability to stimulate cell-mediated and/or humoral immunity against HIV. Specifically *S. cerevisiae* AFY435-gp160-SF2(c) and *S. cerevisiae* AFY435-gp160-SF2(s) yeast vehicles (produced as described in Example 1) were tested, as were the following controls: *S. cerevisiae* intact cell AFY433-vector(c) and *S. cerevisiae* spheroplast AFY433-vector(s) which were comparable to AFY435-gp160-SF2(c) and AFY435-gp160-SF2(s), respectively, except that AFY433-vector(c) and AFY433-vector(s) were transformed with vector alone rather than with vector containing gp160.

B. Administration of yeast vehicles to animals and recovery of spleen and lymph node cells Five groups of two Balb/c mice each were injected intraperitoneally once a week for a total of three weeks with 100 microliters (μl) of injection buffer (1.4M Sorbitol, 5 mM magnesium chloride, 10 mM Tris, pH 7.4) containing the following: for Group 1 (mice 1 and 2), nothing; for Group 2 (mice 3 and 4), about 2×10⁷ AFY433-vector(c) cells; for Group 3 (mice 5 and 6), about 2×10⁷ AFY433-vector(s) spheroplasts; for Group 4 (mice 7 and 8), about 2×10⁷ AFY435-gp160-SF2(c) cells; and for Group 5 (mice 9 and 10), about 2×10⁷ AFY435-gp160-SF2(s) spheroplasts. Fourteen days after their third immunization, all mice were sacrificed by carbon dioxide inhalation.

Blood was obtained from the mice by cardiac puncture and allowed to clot at room temperature. Serum was used for Western-blot and immunoprecipitation analyses.

Spleen and mesenteric lymph node (LN) cells were obtained under aseptic conditions and single cell suspensions obtained by gently pressing the organs through nylon mesh screens. Spleen and lymph node cells from individual mice were pooled and resuspended in TCM tissue culture medium (RPMI 1640 (available from Life Technologies, Gaithersburg, Md.) supplemented with 7.5% fetal calf serum, L-glutamine, L-pyruvate, vitamins, nonessential amino acids, gentamycin and 2-mercaptoethanol). There was no apparent difference in recovery of cells from any of the mice, as shown in Table 1.

TABLE 1

Recovery of cells from mice injected with yeast or spheroplasts.

| Mouse | Treatment | Spleen + LN (10⁶) | Post Ig plates (10⁶) |
|---|---|---|---|
| 1, 2 | Not injected | 184 & 302 | 32 & 26 |
| 3, 4 | Yeast-AFY 433-vector | 306 & 324 | 20 & 20 |
| 5, 6 | Sphero-AFY 433-vector | 240 & 330 | 23 & 27 |
| 7, 8 | Yeast-AFY435-gp160-SF2 | 282 & 315 | 20 & 20 |
| 9, 10 | Sphero-AFY435-gp160-SF2 | 252 & 294 | 21 & 26 |

Spleen and lymph node cells were divided evenly into three groups. The first group was washed and resuspended in Dulbecco's phosphate-buffered saline (available from Life Technologies) and placed in petri dishes to which goat anti-mouse immunoglobulins had been adsorbed. After incubation on ice for about 30 minutes, non-adherent cells (about 90% T cells) were gently removed, washed, and resuspended in TCM for use in T cell proliferation assays as T cell enriched spleen and lymph node cells. Recovery of such cells is indicated in Table 1 in the column entitled "Post Ig plates". The second group of cells were gamma-irradiated (2000 R) for use in T cell proliferation assays as irradiated cells. The third group of cells were left untreated for generation of cytotoxic T lymphocytes (CTL).

In all experiments, data was calculated as the mean∓S.D. for triplicate determinations for each sample point. For proliferation assays, data is expressed as a stimulation index (S.I.) in which an S.I. of 100 is equivalent to the proliferation observed with T cells obtained from unimmunized mice. Thus an S.I. of 150 represents a response which is 50% above background. For CTL assays, data is expressed as corrected cytolysis which takes into account background, or spontaneous, killing.

C. Infection of cells with recombinant vaccinia virus

About 1×10⁶ P815 mouse leukemia cells were incubated overnight in TCM either with about 1×10⁶ plaque forming units (pfu) recombinant vaccinia virus expressing β-galactosidase (Vac-lac) or with about 1×10⁶ pfu recombinant vaccinia virus expressing HIV gp160-SF2 (Vac-SF2; available from Dr. D. Kuritzkes, University of Colorado Health Sciences Center, Denver, Colo.) to produce infected cells denoted P815-Vac-lac and P815-Vac-SF2, respectively. Similarly, about 1×10⁶ BC10ME mouse fibroblast cells were incubated overnight in TCM either with about 1×10⁶ pfu recombinant vaccinia virus expressing β-galactosidase (Vac-lac) or with about 1×10⁶ pfu recombinant vaccinia virus expressing HIV gp160-SF2(Vac-SF2) to produce infected cells denoted BC10ME-Vac-lac and BC10ME-Vac-SF2, respectively. The infected cells were pelleted by centrifugation and resuspended in TCM. For proliferation assays, infected BC10ME cells were heated to 50° C. for 30 min to inactivate any live virus and to provide a source of antigen-containing cell lysate. For CTL assays, infected P815 cells were labeled cytoplasmically with 100 μCi Na₂⁵¹CrO₄ and diluted to 5×10⁴/ml in TCM.

D. Stimulation of a humoral immune response

T cell proliferation assays to detect humoral immune response stimulation in mice administered gp160-expressing yeast vehicles of the present invention were conducted as follows. T cell enriched spleen and lymph node cells, produced as described in Example 2B, were diluted to $4 \times 10^6$ cells/ml in TCM. Unfractionated, irradiated spleen and lymph node cells, produced as described in Example 2B, were diluted to $4 \times 10^6$ cells/ml in TCM. Enriched T cells and irradiated cells from the same mouse were mixed 1:1 such that the final concentration of each cell type was about $2 \times 10^6$ cells/ml. 100 μl of the T cell mixtures were placed in individual wells of 96-well round-bottomed plates which each contained 100 μl of the concentrations of antigens or mitogens in TCM as indicated in Table 2.

TABLE 2

Antigens or mitogens used in assay

| Tube | Antigen or mitogen | Tube | Antigen or mitogen |
|---|---|---|---|
| A | Nil | I | Yeast-433 ($5 \times 10^6$/ml) |
| B | 2C11-anti-CD3 (0.2 μg/ml) | J | Yeast-433 ($1 \times 10^6$/ml) |
| C | H57-anti-TCR (1.0 μg/ml) | K | Sphero-433 ($5 \times 10^6$/ml) |
| D | Concanavalin A (5 μg/ml) | L | Sphero-433 ($1 \times 10^6$/ml) |
| E | gp120-IIIb (1 μg/ml) | M | Yeast-435env ($5 \times 10^6$/ml) |
| F | gp120-IIIb (1 μg/ml) - heated - 50° C., 30' | N | Yeast-435env ($1 \times 10^6$/ml) |
| G | BC10ME-Vac-lac cell lysates - heated - 50° C., 30' | O | Sphero-435env ($5 \times 10^6$/ml)HBC10ME-Vac-SF2 cell lysates - heated - 50° C., 30'PSphero-435env ($1 \times 10^6$/ml) |

Assays were set up in triplicate and T cell proliferation was assessed by thymidine incorporation; on days 3 and 6, 25 μl of $^3$HTdR (40 μCi/ml) were added to each well. About 18 hrs later, the wells were harvested to glass-fiber filters and counted in a scintillation counter.

The results of the T cell proliferation assays are shown in Table 3.

TABLE 3

Day 3 and Day 6 proliferation data where background simulation index (S.I.) for wells without any stimulus = 100.

| Day 3 data Stimulus | Non-inj mice | | Vector control mice | | | SF2 mice | | | |
|---|---|---|---|---|---|---|---|---|---|
| | 1 | 2 | 4 | 5 | 6 | 7 | 8 | 9 | 10 |
| Anti-CD3 | 1781 | 3438 | 1756 | 1909 | 1725 | 2728 | 2720 | 1467 | 1626 |
| Anti-TCR | 737 | 692 | 342 | 295 | 575 | 578 | 1229 | 231 | 451 |
| Con A | 8641 | 8931 | 13548 | 15809 | 7967 | 11885 | 10255 | 9551 | 9184 |
| gp120-IIIb protein | 138 | 62 | 83 | 102 | 100 | 90 | 81 | 99 | 105 |
| gp120-IIIb protein (50° C.; 30') | 155 | 84 | 64 | 78 | 80 | 198 | 186 | 122 | 166 |
| BC10ME-Vac-lac cell lysate | 87 | 134 | 74 | 112 | 91 | 161 | 134 | 92 | 143 |
| BC10ME-Vac-SF2 cell lysate | 158 | 231 | 270 | 203 | 263 | 469 | 422 | 184 | 584 |
| Yeast-vector ($5 \times 10^5$; 50° C.; 30') | 121 | 156 | 533 | 240 | 470 | 369 | 614 | 288 | 463 |
| Yeast ($1 \times 10^5$; 50° C. 30') | 172 | 192 | 363 | 153 | 341 | 265 | 494 | 166 | 280 |
| Sphero ($5 \times 10^5$; 50° C.; 30') | 248 | 275 | 577 | 398 | 896 | 702 | 867 | 380 | 544 |
| Sphero ($1 \times 10^5$; 50° C.; 30') | 177 | 257 | 421 | 176 | 375 | 342 | 489 | 176 | 306 |
| Yeast-SF2 ($5 \times 10^5$; 50° C.; 30') | 110 | 215 | 557 | 360 | 703 | 575 | 749 | 381 | 619 |
| Yeast ($1 \times 10^5$; 50° C.; 30') | 79 | 225 | 291 | 227 | 346 | 411 | 461 | 208 | 278 |
| Sphero ($5 \times 10^5$; 50° C.; 30') | 76 | 115 | 397 | 468 | 527 | 654 | 732 | 336 | 502 |
| Sphero ($1 \times 10^5$; 50° C.; 30') | 112 | 213 | 297 | 201 | 379 | 385 | 480 | 149 | 352 |

| Day 3 data | Non-inj mice | | Vector mice | | | SF2 mice | | | |
|---|---|---|---|---|---|---|---|---|---|
| Stimulus | 1 | 2 | 4 | 5 | 6 | 7 | 8 | 9 | 10 |
| Anti-CD3 | 217 | 359 | 445 | 823 | 273 | 416 | 161 | 786 | 206 |
| Anti-TCR | 280 | 493 | 264 | 219 | 458 | 564 | 380 | 737 | 362 |
| Con A | 277 | 861 | 363 | 1525 | 628 | 897 | 412 | 1648 | 337 |
| gp120-IIIb protein | 73 | 106 | 91 | 110 | 97 | 115 | 159 | 180 | 102 |
| gp120-IIIb protein (50° C.; 30') | 88 | 107 | 108 | 128 | 166 | 173 | 290 | 201 | 203 |
| BC10ME-Vac-lac cell lysate | 104 | 85 | 95 | 195 | 117 | 134 | 100 | 227 | 99 |
| BC10ME-Vac-SF2 cell lysate | 99 | 73 | 99 | 217 | 109 | 248 | 313 | 218 | 289 |
| Yeast-vector ($5 \times 10^5$; 50° C.; 30') | 137 | 101 | 931 | 510 | 762 | 850 | 822 | 1737 | 1238 |
| Yeast ($1 \times 10^5$; 50° C. 30') | 117 | 248 | 616 | 291 | 503 | 526 | 763 | 434 | 581 |
| Sphero ($5 \times 10^5$; 50° C.; 30') | 287 | 397 | 1185 | 1157 | 991 | 814 | 775 | 1376 | 674 |
| Sphero ($1 \times 10^5$; 50° C.; 30') | 158 | 175 | 845 | 313 | 351 | 373 | 755 | 691 | 567 |
| Yeast-SF2 ($5 \times 10^5$; 50° C.; 30') | 319 | 235 | 1049 | 836 | 950 | 889 | 1296 | 1864 | 1249 |
| Yeast ($1 \times 10^5$; 50° C.; 30') | 126 | 227 | 1001 | 379 | 597 | 507 | 790 | 605 | 508 |
| Sphero ($5 \times 10^5$; 50° C.; 30') | 189 | 150 | 1497 | 957 | 1127 | 902 | 1720 | 942 | 1135 |
| Sphero ($1 \times 10^5$; 50° C.; 30') | 149 | 243 | 1136 | 242 | 378 | 525 | 1179 | 301 | 438 |

In the proliferation data shown in Table 3, it is important to note that all of the mice responded comparably to the mitogenic stimuli provided by anti-CD3 and anti-TCR antibodies and concanavalin A. These mitogens were included in the assay to estimate whether the same number of responding T cells from each mouse were added to the cultures. The lack of response to any stimulus in wells containing cells from mouse 3 for unknown reasons.

Some of the results of the T cell proliferation assays are also depicted in FIG. 1. FIG. 1A depicts T cell proliferation results at day 3 in response to gp120 protein from HIV strain IIIb (i.e., gp120-IIIb protein). FIG. 1B depicts T cell proliferation results at day 3 in response to lysates from BC10ME cells infected with Vac-SF2. FIG. 1C depicts T cell proliferation results at day 6 in response to gp120-IIIb protein. FIG. 1D depicts T cell proliferation results at day 6 in response to lysates from BC10ME cells infected with Vac-SF2. FIG. 1E depicts T cell proliferation results at day 3 in response to intact AFY433 vector control yeast (i.e., S. cerevisiae AFY433-vector(c). FIG. 1F depicts T cell proliferation results at day 6 in response to intact AFY433 vector control yeast.

T cells from mice immunized with live intact yeast expressing HIV gp160-SF2 (mice 7 and 8) or with spheroplasts expressing HIV gp160-SF2 (mice 9 and 10) proliferated in response to gp120, whereas T cells from non-immunized animals (mice 1 and 2) or from animals immunized with live intact control yeast (mice 3 and 4) or spheroplasts (mice 5 and 6) did not proliferate in response to gp120; see Table 3 and FIG. 1A through 1D. T cells isolated from mice 7, 8, 9 and 10 responded to HIV gp160 in the form of either purified protein (see Table 3 and FIGS. 1A and 1C) or as lysates of cells infected with a recombinant vaccinia virus encoding gp160-SF2 (see Table 3 and FIGS. 1B and 1D). Responses were observed both on day 3 and on day 6. It is of particular note that even though the mice were immunized against gp160 derived from the SF2 strain of HIV, their T cells showed a low but significant response to gp120 protein isolated from the HIV IIIb strain.

The results shown in FIGS. 1E and 1F indicate that T cells isolated from each of the immunized mice (i.e., mice 3, 4, 5, 6, 7, 8, 9 and 10) responded to control AFY433-vector(c) intact yeast in a dose-dependent fashion. The day 6 response was very high. Such T cells also responded to AFY433-vector(s) as well as to AFY435-gp160-SF2(c) and AFY435-gp160-SF2(s) yeast vehicles; see Table 3.

Figure 2:
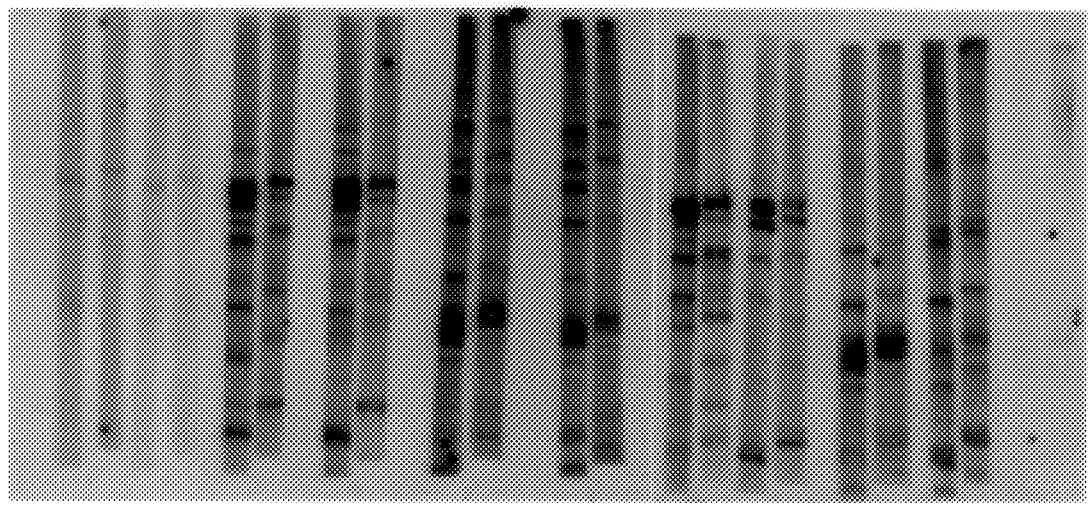
FIG. 2 depicts a Western blot of sera isolated from mice administered yeast vehicles of the present invention.

The overall immune response generated by mice in response to being administered AFY433-vector(c), AFY433-vector(s), AFY435-gp160-SF2(c) and AFY435-gp160-SF2(s) was determined by Western blot analysis of serum collected from each of the mice, using techniques known to those skilled in the art. The results are shown in FIG. 2. Briefly, lanes 1, 3, 5, 7, 9, 11, 13, 15, 17, 19, and 21 represent lanes of a gel that were each loaded with about 100 μg of protein from AFY435-gp160-SF2 yeast lysates; whereas lanes 2, 4, 6, 8, 10, 12, 14, 16, 18 and 20 represent lanes of a gel that were each loaded with about 100 μg of AFY433-vector yeast lysates. The numbered lanes were blotted with serum samples from the following mice: lane 1, from mouse 1; lanes 2 and 3, from mouse 2; lanes 4 and 5, from mouse 3; lanes 6 and 7 from mouse 4; lanes 8 and 9, from mouse 5; lanes 10 and 11, from mouse 6; lanes 12 and 13, from mouse 7; lanes 14 and 15, from mouse 8; lanes 16 and 17, from mouse 9; and lanes 18 and 19, from mouse 10. Lanes 20 and 21 were blotted with antiserum collected from a rabbit immunized with a gp120 fusion protein. This study indicated that the immunized mice made antibodies to a variety of yeast-derived proteins and that the pattern of proteins recognized by mouse serum was dependent on whether the mice had been immunized with intact yeast or spheroplasts. Humoral immune responses generated by mice 7, 8, 9 and 10 in response to gp160 could not be distinguished in this Western blot due to the high background reactivity of antisera generated in response to other yeast antigens, and because of the relatively low abundance of gp160 recovered from yeast lysates in this experiment.

In summary, yeast vehicles introduced systemically into mice stimulated a vigorous immune response against proteins of the yeast vehicle, including the production of T cells capable of proliferating in response to the heterologous protein carried by the yeast vehicle.

E. Stimulation of a cell-mediated immune response

CTL assays were conducted to detect cell-mediated immune response stimulation in mice administered gp160-expressing yeast vehicles of the present invention. CTL were generated by techniques known to those skilled in the art. Briefly, about $40 \times 10^6$ unfractionated, unirradiated spleen and lymph node cells were placed in flasks containing about $1 \times 10^7$ AFY435-gp160-SF2(c) plus about $1 \times 10^7$ AFY435-gp160-SF2(s) yeast vehicles in a total of 10 ml TCM and cultured for 7 days. Flasks were set up in duplicate with one getting 5% cell free supernatants from concanavalin A-stimulated rat spleen cells (CAS) as a source of T cell growth factors at the start of the culture period. On day 5, 5% CAS was added to all flasks. CTL were harvested by ficoll/hypaque density gradient centrifugation and resuspended in TCM for use.

The CTL assay was conducted according to standard techniques. Briefly, CTL were diluted to concentrations of about 2×10⁷ cells/ml and about 1×10⁷ cells/ml in TCM. 100 μl of CTL and 100 μl of $^{51}$Cr-labeled target cells were mixed together, in triplicate, in 96 well V-bottomed plates. Cytolysis was determined by release of radioactive chromium from the target cells after 4 hrs incubation at 37° C.

CTL were assayed on five target cell populations: P815, P815-Vac-Lac, P815-Vac-SF2, BC10ME and BC10ME-gp160-IIIb (transfected BC10ME cells engineered to express gp160-IIIb). Percent lysis values were obtained for each CTL-target cell combination at two effector:target (E:T) ratios. Using standard methods for CTL assays, data was corrected for nonspecific lysis on P815-Vac-lac for P815Vac-SF2 and on BC10ME for BC10ME-gp160-IIIb. The results are shown in Table 4.

TABLE 4

CTL assay data

| Mouse | CAS | P815-Vac-SF2 Corrected % lysis | | BC10ME-gp160-IIIb Corrected % lysis | |
|---|---|---|---|---|---|
| | | Target 40:1 | 20:1 | Target 40:1 | 20:1 |
| 1 | day 5 | 0 | 2 | −4 | −4 |
| | day 1 | 0 | −4 | −3 | −5 |
| 2 | day 5 | 1 | −1 | −5 | −6 |
| | day 1 | −4 | 4 | −5 | −9 |
| 3 | day 5 | nd | nd | nd | nd |
| | day 1 | nd | nd | nd | nd |
| 4 | day 5 | nd | nd | nd | nd |
| | day 1 | 0 | 3 | −8 | −6 |
| 5 | day 5 | nd | nd | nd | nd |
| | day 1 | nd | nd | nd | nd |
| 6 | day 5 | −1 | −4 | −5 | −1 |
| | day 1 | −1 | 5 | −7 | −8 |
| 7 | day 5 | 34 | 20 | −6 | −8 |
| | day 1 | 51 | 39 | −9 | −8 |
| 8 | day 5 | 25 | 7 | 10 | 3 |
| | day 1 | 36 | 24 | 17 | 3 |
| 9 | day 5 | −6 | −2 | −8 | −9 |
| | day 1 | 12 | −3 | 2 | −7 |
| 10 | day 5 | 19 | 17 | 18 | 10 |
| | day 1 | 44 | 33 | 26 | 11 |

Figure 3:
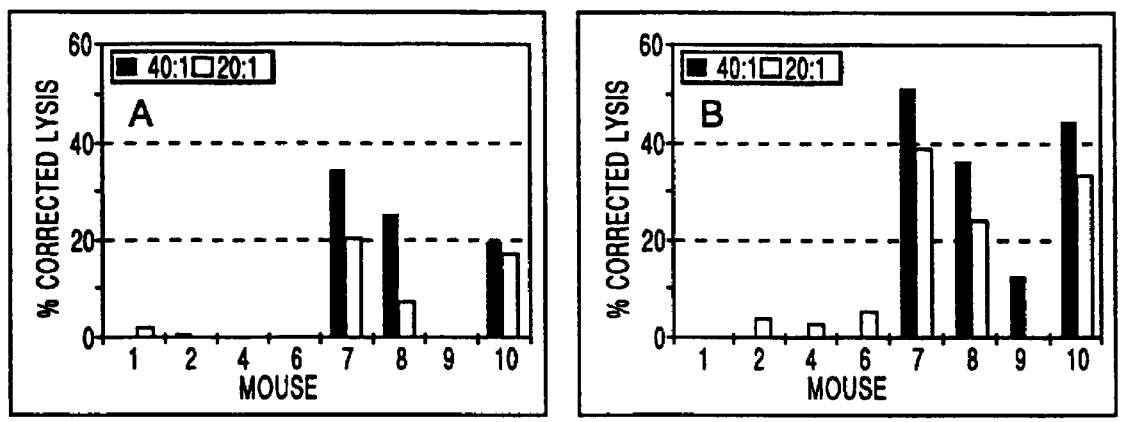
FIGS. 3A & B includes graphs depicting selective killing by cytotoxic T cells generated from mice administered yeast vehicles of the present invention.

CTL generated from mice immunized with AFY435-gp160-SF2(c) and AFY435-gp160-SF2(s) yeast vehicles were able to kill target cells expressing gp160-SF2 and, to a much lesser extent, cells expressing gp160-IIIb. Killing showed a dose-response in terms of E:T ratio in that at the higher E:T ratio, more target cells were killed. Killing of P815-Vac-SF2 cells by CTL generated from mice immunized with AFY435-gp160-SF2(c) and AFY435-gp160-SF2 (s) yeast vehicles is shown in FIG. 3. FIGS. 3A and 3B depict results from separate assays in which CAS was added, respectively, on day 5 and day 1.

No data is shown for CTL derived from mice 3 and 5, since very few cells were recovered from these flasks. Nonetheless, the data are convincing that intact yeast and/or spheroplasts derived from yeast expressing a heterologous protein can be used to prime T cells in vitro and in vivo to kill cells expressing the heterologous protein.

The results obtained in this controlled study correlate well with results obtained in earlier pilot experiments. In the earlier assays, CTL generated from mice immunized with either AFY435-gp160-SF2(c) or AFY435-gp160-SF2(s) yeast vehicles were able to kill P815-Vac-SF2 cells, whereas CTL derived from non-immunized mice could not. In both the pilot and controlled studies, the degree of killing was similar, and it appeared that animals injected with intact yeast gave rise to stronger CTL than mice injected with spheroplasts.

F. The results reported in this Example indicate that yeast vehicles of the present invention can prime mouse T cells to respond to a heterologous protein For example:

(a) T cells isolated from the spleen and lymph nodes of mice injected intraperitoneally with yeast vehicles expressing the HIV envelope protein gp160-SF2 proliferated in vitro in response to extracts of cells infected with a recombinant vaccinia virus encoding gp160-SF2. T cells derived from non-immunized mice or mice which had been immunized with recombinant yeast containing vector DNA but not DNA encoding gp160-SF2 did not proliferate in response to such cell extracts.

(b) Spleen and lymph node cells from mice immunized with yeast vehicles expressing the HIV envelope protein gp160-SF2 contained cytotoxic T cells precursors which, following in vitro stimulation, could specifically kill cells infected with a recombinant vaccinia virus encoding gp160-SF2. T cells derived from non-immunized mice or mice which had been immunized with yeast containing vector DNA but not DNA encoding gp160-SF2 did not contain gp160-SF2-primed CTL precursors.

(c) T cells from the mice immunized with yeast vehicles expressing the HIV envelope protein gp160-SF2 also proliferated to a lesser, but significant, degree in response to purified gp120 protein derived from a different HIV clade, IIIb (LAI). CTL derived from these animals also showed demonstrable cross-reactivity to cells expressing gp120-IIIb. These results suggest that yeast vehicles expressing an HIV gp160 protein may induce cross-reactive immunity to gp160 proteins of other HIV isolates.

(d) Mice injected with spheroplasts derived from intact AFY435-gp160-SF2 yeast also responded in proliferation and cytotoxic assays to gp160-SF2 as well as to gp120-IIIb protein suggesting that spheroplasts could be used for immunization in place of intact yeast.

(e) Immunization with intact yeast or spheroplasts did not require administration of an adjuvant. Mice injected intraperitoneally with the intact yeast or spheroplasts did not show any adverse effects even upon repeated injections.

In summary, not only were T cell proliferative responses elicited (indicative of helper T cell priming) but CTL activity (indicative of cell-mediated immunity) was also induced. The priming of CTL activity suggests a unique handling of yeast by the immune system (demonstrated for intact yeast and spheroplasts) which results in antigen presentation via both class II (to helper T cells) and class I (to CTL precursors). Priming of both types of T cells occurred in the absence of adjuvant suggesting that yeast vehicles may function as their own adjuvants. Furthermore, immunized mice showed no typical adjuvant reactions (i.e., undesirable side effects) upon injection of intact yeast or spheroplasts, demonstrating the safety of yeast vehicles of the present invention.

Example 3

This example demonstrates that a yeast vehicle of the present invention is safe, even in an immunocompromised animal, such as in a SCID mouse which is deficient in both T and B lymphocytes.

Two CB.17$^{Scid}$ mice (available from Jackson Labs, Bar Harbor, Me.) were injected intraperitoneally with about 2×10⁷ AFY435-gp160-SF2(c) in 100 μl injection buffer.

Two additional CB.17$^{scid}$ mice were injected intraperitoneally with about 2×10$^7$ AFY435-gp160-SF2(s) in 100 μl injection buffer. The immunized mice exhibited no adverse reactions at the site of injection or overall health changes over a 10-day period during which the mice were monitored daily.

On day 10 after injection, mice were sacrificed by carbon dioxide inhalation. Peritoneal lavage was performed using 5 ml of sterile PBS (phosphate-buffered saline). About 200 μl of lavage from each mouse were applied to separate petri dishes containing rich medium (e.g., yeast potato dextrose medium) or selective defined medium for yeast growth. The petri dishes were incubated at room temperature for 7 days, during which time no outgrowth of yeast was observed. Control plates containing samples of the yeast preparations used for the injections showed growth indicating that the mice had been injected with live yeast.

These experiments demonstrate the safety of yeast vehicles of the present invention, even in immunodeficient animals.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A method to elicit an antigen-specific humoral immune response and an antigen-specific cell-mediated immune response in a mammal, said method comprising administering to said mammal a yeast selected from the group consisting of a yeast microorganism and a yeast spheroplast, said yeast being transformed with a heterologous nucleic acid molecule encoding an antigen, wherein said antigen has been expressed by said yeast; and wherein said antigen which has been expressed by said yeast elicits an antigen-specific humoral immune response and an antigen-specific cell-mediated immune response in said mammal.

2. The method of claim 1, wherein said yeast is transformed with said nucleic acid molecule by a technique selected from the group consisting of diffusion, active transport, liposome fusion, electroporation, bath sonication, and genetic engineering.

3. The method of claim 1, wherein said antigen is selected from the group consisting of viral antigens, mammalian cell surface molecules, bacterial antigens, fungal antigens, protozoan antigens helminth antigens, ectoparasite antigens, and cancer antigens.

4. The method of claim 1, wherein said yeast is a nonpathogenic yeast.

5. The method of claim 1, wherein said yeast is of a genus selected from the group consisting of Saccharomyces, Candida, Cryptococcus, Hansenula, Kluyveromyces, Pichia, Rhodotorula, Schizosaccharomyces and Yarrowia.

6. The method of claim 1, wherein said yeast is of a genus selected from the group consisting of Saccharomyces, Candida, Hansenula, Pichia and Schizosaccharomyces.

7. The method of claim 1, wherein said yeast is of a species selected from the group consisting of *Saccharomyces cerevisiae, Candida albicans, Hansenula polymorpha, Pichia pastoris* and *Schizosaccharomyces pombe.*

8. The method of claim 1, wherein said yeast is of the species *Saccharomyces cerevisiae.*

9. The method of claim 1, wherein said yeast is administered by a route selected from the group consisting of bronchial, genital, inhalatory, nasal, oral, parenteral and rectal routes.

10. The method of claim 1, wherein said yeast is administered with a pharmaceutically acceptable excipient.

11. The method of claim 1, wherein said yeast is administered with a member selected from the group consisting of adjuvants and carriers.

12. A pharmaceutical composition comprising:

(a) a yeast selected from the group consisting of a yeast microorganism and a yeast spheroplast, said yeast being transformed with a heterologous nucleic acid molecule encoding an antigen operatively linked to a transcription control sequence, wherein said yeast has expressed said antigen; and (b) a pharmaceutically acceptable excipient;

wherein said antigen which has been expressed by said yeast elicits an antigen-specific humoral immune response and an antigen-specific cell-mediated immune response when administered to a mammal.

* * * * *

UNITED STATES PATENT AND TRADEMARK OFFICE
CERTIFICATE OF CORRECTION

PATENT NO. : 5,830,463
DATED : November 3, 1998
INVENTOR(S) : Duke, et. al.

It is certified that error appears in the above-identified patent and that said Letters Patent is hereby corrected as shown below:

Claim 1, line 34, after "antigen" and before the comma, add --"operatively linked to a transcription control sequence"

Signed and Sealed this

Ninth Day of March, 1999

Attest:

Attesting Officer

Q. TODD DICKINSON

Acting Commissioner of Patents and Trademarks